US012779202B2

(12) United States Patent
Boyce et al.

(10) Patent No.: US 12,779,202 B2
(45) Date of Patent: Nov. 3, 2026

(54) CATHETER BLOOD PUMPS WITH PRESSURE SENSORS AND RELATED METHODS OF DETERMINING POSITIONING

(71) Applicant: FBR Medical, Inc., El Dorado Hills, CA (US)

(72) Inventors: Andrew J. Boyce, Laguna Woods, CA (US); Bradley J. Sargent, Mission Viejo, CA (US); Peter G. Piferi, Orange, CA (US)

(73) Assignee: FBR MEDICAL, INC., El Dorado Hills, CA (US)

( * ) Notice: Subject to any disclaimer, the term of this patent is extended or adjusted under 35 U.S.C. 154(b) by 467 days.

(21) Appl. No.: 18/335,247

(22) Filed: Jun. 15, 2023

(65) Prior Publication Data

US 2023/0405303 A1 Dec. 21, 2023

Related U.S. Application Data

(60) Provisional application No. 63/374,426, filed on Sep. 2, 2022, provisional application No. 63/352,932, filed (Continued)

(51) Int. Cl.
*A61M 60/122* (2021.01)
*A61M 25/00* (2006.01)
(Continued)

(52) U.S. Cl.
CPC ...... *A61M 60/508* (2021.01); *A61M 25/0026* (2013.01); *A61M 60/13* (2021.01); *A61M 60/216* (2021.01); *A61M 60/438* (2021.01)

(58) Field of Classification Search
CPC ............................ A61M 60/13; A61M 60/531
See application file for complete search history.

(56) References Cited

U.S. PATENT DOCUMENTS 3,510,229 A 5/1970 Smith
4,187,879 A 2/1980 Fermer et al.
(Continued)

FOREIGN PATENT DOCUMENTS

CN 111773460 A 10/2020
CN 111840681 A 10/2020
(Continued)

OTHER PUBLICATIONS

FISO Technologies Inc. "Medical Pressure Monitoring" (10 pages) retrieved from https://fiso.com/wp-content/uploads/2018/10/MC-00263_-Medical-Pressure-Monitoring-Product-Datasheet_R7.pdf on Jun. 8, 2023.

(Continued)

*Primary Examiner* — Michael J D'Abreu
(74) *Attorney, Agent, or Firm* — Myers Bigel, P.A.

(57) ABSTRACT

Catheter blood pumps with an inlet cage, cannula, impeller assembly and a multiple lumen shaft that is coupled to a that provides connectors that connect to external components. First and second fiberoptic pressure sensors extend inside and along a length of the multi-lumen catheter. The first fiberoptic pressure sensor is longer than the second fiberoptic pressure sensor and extends longitudinally distal to the multi-lumen catheter to terminate at a distal end portion of the cannula, proximal to the inlet cage. The sensor heads of the first fiberoptic pressure sensor and the second fiberoptic pressure sensor are exposed to local environmental conditions. The sensor head of the second fiberoptic pressure sensor can terminate proximal to the impeller cage windows. A pressure differential identified by a difference in pressure provided by the first and second fiberoptic pressure sensors can be used to confirm proper placement during intravascular placement into the heart.

28 Claims, 15 Drawing Sheets

Related U.S. Application Data on Jun. 16, 2022, provisional application No. 63/352,907, filed on Jun. 16, 2022.

(51) Int. Cl.

| | |
|---|---|
| ***A61M 60/13*** | (2021.01) |
| ***A61M 60/216*** | (2021.01) |
| ***A61M 60/438*** | (2021.01) |
| ***A61M 60/508*** | (2021.01) |

(56) References Cited

U.S. PATENT DOCUMENTS 4,625,712 A 12/1986 Wampler
4,753,221 A 6/1988 Kensey et al.
4,817,586 A 4/1989 Wampler
4,846,152 A 7/1989 Wampler et al.
4,919,647 A 4/1990 Nash
4,969,865 A 11/1990 Hwang et al.
5,092,844 A 3/1992 Schwartz et al.
5,112,292 A 5/1992 Hwang et al.
5,163,910 A 11/1992 Schwartz et al.
5,169,378 A 12/1992 Figuera
5,376,114 A 12/1994 Jarvik
5,405,383 A 4/1995 Barr
5,588,812 A 12/1996 Taylor et al.
5,749,855 A 5/1998 Reitan
5,755,784 A 5/1998 Jarvik
5,776,190 A 7/1998 Jarvik
5,888,241 A 3/1999 Jarvik
5,911,685 A 6/1999 Siess et al.
6,007,478 A 12/1999 Siess et al.
6,053,907 A 4/2000 Zirps
6,058,593 A 5/2000 Siess
6,076,958 A 6/2000 Althouse et al.
6,135,943 A 10/2000 Yu et al.
6,139,487 A 10/2000 Siess
6,176,822 B1 1/2001 Nix et al.
6,176,848 B1 1/2001 Rau et al.
6,200,260 B1 3/2001 Bolling
6,227,820 B1 5/2001 Jarvik
6,245,007 B1 6/2001 Bedingham et al.
6,295,877 B1 10/2001 Aboul-Hosn et al.
6,299,575 B1 10/2001 Bolling
6,327,994 B1 12/2001 Labrador
6,387,037 B1 5/2002 Bolling et al.
6,390,969 B1 5/2002 Bolling et al.
6,406,422 B1 6/2002 Landesberg
6,428,464 B1 8/2002 Bolling
6,497,698 B1 12/2002 Fonger et al.
6,508,787 B2 1/2003 Erbel et al.
6,527,699 B1 3/2003 Goldowsky
6,533,716 B1 3/2003 Schmitz-Rode et al.
6,544,216 B1 4/2003 Sammler et al.
6,620,004 B1 9/2003 Piper
6,623,475 B1 9/2003 Siess
6,644,125 B1 11/2003 Siess et al.
6,685,621 B2 2/2004 Bolling et al.
6,685,696 B2 2/2004 Fleischhacker et al.
6,716,157 B2 4/2004 Goldowsky
6,719,720 B1 4/2004 Voelker et al.
6,790,171 B1 9/2004 Gruendeman et al.
6,794,789 B2 9/2004 Siess et al.
6,808,483 B1 10/2004 Ortiz et al.
6,889,082 B2 5/2005 Bolling et al.
6,942,611 B2 9/2005 Siess
6,981,942 B2 1/2006 Khaw et al.
7,010,954 B2 3/2006 Siess et al.
7,011,620 B1 3/2006 Siess
7,022,100 B1 * 4/2006 Aboul-Hosn ....... A61M 60/865 604/6.11
7,027,875 B2 4/2006 Siess et al.
7,070,555 B2 7/2006 Siess
RE39,217 E 8/2006 Rockwood
7,241,257 B1 7/2007 Ainsworth et al.
7,258,679 B2 8/2007 Moore et al.
7,371,210 B2 5/2008 Brock et al.
7,393,181 B2 7/2008 McBride et al.
7,828,710 B2 11/2010 Shifflette
8,037,713 B2 10/2011 Haley et al.
8,079,948 B2 12/2011 Shifflette
8,177,703 B2 5/2012 Smith et al.
8,252,014 B2 8/2012 Fisher
8,298,169 B2 10/2012 Yacoubian et al.
8,485,961 B2 7/2013 Campbell et al.
8,579,858 B2 11/2013 Reitan et al.
8,591,170 B1 11/2013 Rawls
8,591,393 B2 11/2013 Walters et al.
8,597,170 B2 12/2013 Walters et al.
8,617,239 B2 12/2013 Reitan
8,684,904 B2 4/2014 Campbell et al.
8,721,517 B2 5/2014 Zeng et al.
8,777,832 B1 7/2014 Wang et al.
8,795,576 B2 8/2014 Tao et al.
8,814,776 B2 8/2014 Hastie et al.
8,849,398 B2 9/2014 Evans
8,926,492 B2 1/2015 Scheckel
9,028,392 B2 5/2015 Shifflette
9,089,634 B2 7/2015 Schumacher et al.
9,278,189 B2 3/2016 Corbett
9,402,942 B2 8/2016 Hastie et al.
9,433,713 B2 9/2016 Corbett et al.
9,446,179 B2 9/2016 Keenan et al.
9,474,840 B2 10/2016 Siess
9,572,915 B2 2/2017 Heuring et al.
9,669,142 B2 6/2017 Spanier et al.
9,669,144 B2 6/2017 Spanier et al.
9,717,833 B2 8/2017 Mcbride et al.
9,750,861 B2 9/2017 Hastie et al.
9,770,543 B2 9/2017 Tanner et al.
9,814,814 B2 11/2017 Corbett et al.
9,821,100 B2 11/2017 Corbett et al.
9,833,550 B2 12/2017 Siess
9,872,947 B2 1/2018 Keenan et al.
9,872,948 B2 1/2018 Siess
9,878,079 B2 1/2018 Pfeffer et al.
9,895,475 B2 2/2018 Toellner et al.
9,907,890 B2 3/2018 Muller
9,962,475 B2 5/2018 Campbell et al.
9,999,714 B2 6/2018 Spanier et al.
10,018,096 B2 7/2018 Wallimann et al.
10,029,037 B2 7/2018 Muller et al.
10,201,645 B2 2/2019 Muller
10,342,906 B2 7/2019 D'Ambrosio et al.
10,617,808 B2 4/2020 Hastie et al.
10,668,195 B2 6/2020 Flores
10,737,008 B2 8/2020 Corbett et al.
10,808,704 B2 10/2020 Siess et al.
10,905,808 B2 2/2021 Tuval et al.
11,160,970 B2 11/2021 Muller et al.
11,298,524 B2 4/2022 El Katerji et al.
11,305,105 B2 4/2022 Corbett et al.
11,491,322 B2 11/2022 Muller et al.
2002/0150463 A1 10/2002 Deblanc et al.
2003/0105383 A1 6/2003 Barbut et al.
2003/0135086 A1 7/2003 Khaw et al.
2003/0163019 A1 8/2003 Goldowsky
2004/0241019 A1 12/2004 Goldowsky
2005/0049696 A1 3/2005 Siess et al.
2006/0008349 A1 1/2006 Khaw
2006/0041293 A1 * 2/2006 Mehdizadeh .......... A61N 1/056 607/116
2006/0062672 A1 3/2006 McBride et al.
2006/0155158 A1 7/2006 Aboul-Hosn
2006/0161107 A1 * 7/2006 Mantle ...................... A61F 7/12 604/113
2008/0103591 A1 5/2008 Siess
2008/0114339 A1 5/2008 McBride et al.
2009/0069854 A1 3/2009 Keidar et al.
2012/0059460 A1 3/2012 Reitan
2012/0178986 A1 7/2012 Campbell et al.
2013/0053623 A1 2/2013 Evans et al.
2014/0275726 A1 9/2014 Zeng
2015/0080743 A1 * 3/2015 Siess .................. A61M 60/139 600/478

(56) References Cited

U.S. PATENT DOCUMENTS

| | | | |
|---|---|---|---|
| 2015/0247503 | A1 | 9/2015 | Seiss et al. |
| 2015/0290372 | A1 | 10/2015 | Muller et al. |
| 2015/0297812 | A1 | 10/2015 | Miyakoshi et al. |
| 2015/0306291 | A1 | 10/2015 | Bonde et al. |
| 2017/0072120 | A1 | 3/2017 | Tanner et al. |
| 2018/0055979 | A1 | 3/2018 | Corbett et al. |
| 2018/0110908 | A1 | 4/2018 | Larose |
| 2018/0169312 | A1 | 6/2018 | Barry |
| 2019/0046703 | A1 | 2/2019 | Shambaugh et al. |
| 2019/0083690 | A1 | 3/2019 | Siess et al. |
| 2019/0269840 | A1 | 9/2019 | Tuval et al. |
| 2019/0321529 | A1 | 10/2019 | Korakianitis et al. |
| 2019/0365973 | A1 | 12/2019 | Flores |
| 2020/0268952 | A1 | 8/2020 | Nitzan et al. |
| 2020/0405926 | A1 | 12/2020 | Alexander et al. |
| 2021/0008261 | A1 | 1/2021 | Calomeni et al. |
| 2021/0052795 | A1 | 2/2021 | Roehn et al. |
| 2021/0162196 | A1 | 6/2021 | Georges et al. |
| 2021/0170081 | A1 | 6/2021 | Kanz |
| 2021/0187274 | A1 | 6/2021 | Malkin et al. |
| 2021/0196941 | A1 | 7/2021 | Bernazani |
| 2021/0220634 | A1 | 7/2021 | Cook |
| 2021/0260358 | A1 | 8/2021 | Korakianitis et al. |
| 2021/0330958 | A1 | 10/2021 | Stotz et al. |
| 2022/0184377 | A1 | 6/2022 | Almedhychy et al. |
| 2022/0288381 | A1 | 9/2022 | Siess et al. |
| 2022/0313980 | A1 | 10/2022 | Hildebrand et al. |
| 2022/0347458 | A1 | 11/2022 | Spanier |
| 2023/0008168 | A1 | 1/2023 | Piferi |
| 2023/0049460 | A1 | 2/2023 | Skrzypczak et al. |
| 2023/0063196 | A1 | 3/2023 | Spanier et al. |
| 2023/0114252 | A1 | 4/2023 | Butler |
| 2023/0132235 | A1 | 4/2023 | Butler et al. |
| 2023/0144756 | A1 | 5/2023 | Ship |
| 2023/0149699 | A1 | 5/2023 | Beekman et al. |

FOREIGN PATENT DOCUMENTS

| | | | |
|---|---|---|---|
| CN | 212940997 | U | 4/2021 |
| CN | 114602055 | A | 6/2022 |
| WO | 9639956 | A1 | 12/1996 |
| WO | 9853864 | A1 | 12/1998 |
| WO | 0043053 | A1 | 7/2000 |
| WO | 0117581 | A2 | 3/2001 |
| WO | 0121249 | A1 | 3/2001 |
| WO | 0139817 | A2 | 6/2001 |
| WO | 0174419 | A1 | 10/2001 |
| WO | 0241935 | A1 | 5/2002 |
| WO | 0243791 | A1 | 6/2002 |
| WO | 0245775 | A2 | 6/2002 |
| WO | 03103745 | A2 | 12/2003 |
| WO | 2006051023 | A1 | 5/2006 |
| WO | 2007112033 | A2 | 10/2007 |
| WO | 2011039091 | A1 | 4/2011 |
| WO | 2017162618 | A1 | 9/2017 |
| WO | 2018226991 | A1 | 12/2018 |
| WO | 2021119478 | A1 | 6/2021 |
| WO | 2021191106 | A1 | 9/2021 |
| WO | 2022056542 | A1 | 3/2022 |
| WO | 2022204400 | A1 | 9/2022 |
| WO | 2023092122 | A1 | 5/2023 |

OTHER PUBLICATIONS

Abiomed "Automated Impella Controller™ (AIC): Understanding and Navigating the Placement Screen" https://www.heartrecovery.com/education/education-library/abiomed-automated-impella-controller-aic (3 pages) (2023).

Capoccia, Massimo "Mechanical Circulatory Support for Advanced Heart Failure: Are We about to Witness a New 'Gold Standard'?" Journal of Cardiovascular Development and Disease, 3(35):1-22 (2016).

Impella "Protected PCI with the Impella Heart Pump" Patient Brochure Guide https://www.abiomed.com/products-and-services/impella/impella-cp-with-smartassist (16 pages) (2023).

Mendes et al. "Two Years of Experience in the Implantation of Heartmate III" Rev Port Cir Cardiotorac Vasc, 24 (3-4):120 (2017).

Pesarini et al. "Impella-protected PCI: the clinical results achieved so far" Minerva Cardioangiologica, 66(5):612-618 (2018).

Siegenthaler et al. "The Impella Recover microaxial left ventricular assist device reduces mortality for postcardiotomy failure: a three-center experience" J Thorac Cardiovasc Surg, 127(3):812-822 (2004).

* cited by examiner

CATHETER BLOOD PUMPS WITH PRESSURE SENSORS AND RELATED METHODS OF DETERMINING POSITIONING

RELATED APPLICATIONS

This application claims priority to and the benefit of U.S. Provisional Patent Application Ser. No. 63/352,907 filed Jun. 16, 2022, U.S. Provisional Patent Application Ser. No. 63/352,932 filed Jun. 16, 2022, and U.S. Provisional Patent Application Ser. No. 63/374,426 filed Sep. 2, 2022, the contents of which are hereby incorporated by reference as if recited in full herein.

FIELD

This invention relates generally to catheter blood pumps.

BACKGROUND

Some patients who have heart failure, and some of those at risk for developing it, receive interventions intended to temporarily assist the heart before or during a medical or surgical procedure and/or during a recovery period. The intervention typically lasts for less than a week but can continue for several weeks. These interventions include pharmaceuticals and/or medical devices, including cardiac-assist devices.

Some cardiac-assist devices include a pump to supplement the heart's pumping action. By assuming some of the heart's pumping function, these "blood pumps" unload the heart, helping it to recover. Cardiac-assist devices can be temporary or permanent.

Some blood pumps have an extracorporeal (i.e., outside the body) impeller to drive blood flow. Some of these extracorporeal blood pumps connect to a patient's heart and blood vessels directly through the exposed chest using relatively large-diameter tubes (cannulas). Such procedures, performed by cardiac surgeons, are invasive and may require cardiopulmonary bypass. They are, unfortunately, associated with significant complications. Some other extracorporeal blood pumps connect to the patient using relatively wide catheters or cannulas, inserted through peripheral blood vessels.

Some other blood pumps are percutaneous, wherein the impeller (and in some devices, the pump's motor) temporarily reside within the patient. These blood pumps are often coupled to a catheter and are consequently referred to as "catheter blood pumps." Some catheter blood pumps are inserted into the patient using established cath-lab techniques, wherein they are advanced through the vascular system (typically the femoral artery) to a patient's heart. This approach is significantly less invasive than cardiac surgery or other relatively complicated procedures.

It is desirable for a catheter blood pump to have as small a diameter as possible to minimize trauma to the vasculature or trauma associated with the surgery performed for minimally invasive insertion into position. It is also desirable for such a pump to have a large pumping capacity, preferably 2 liters per minute or even more, to provide sufficient circulation for a patient, if such a rate can be provided without causing undesired performance issues. Such a pump must avoid, to the extent possible, damaging the blood in the form of hemolysis (i.e., destruction of red blood cells).

Intravascular blood pumps comprise miniaturized blood pumps capable of being percutaneously or surgically introduced into the vascular system of a patient, typically to provide left and/or right heart support. See, e.g., U.S. Pat. No. 4,625,712 which describes a multiple stage intravascular axial-flow blood pump which can be percutaneously inserted into an artery for heart assist and U.S. Pat. No. 4,846,152 which describes a single-stage intravascular axial flow blood pump, the contents of which are hereby incorporated by reference as if recited in full herein. These blood pumps position the drive unit/motor outside the body (extracorporeal) and use long cable drive systems. The maneuverability and/or durability of these types of blood pumps was often less than desired. During use, components of these devices tended to deteriorate prematurely due to rotational and pulsatile forces experienced by the blood pumps.

Other intravascular blood pumps are configured so that the drive unit/motor and the impeller are directly connected to each other, with the motor and the impeller (pump) housing having the substantially the same outer diameter. See, e.g., U.S. Pat. No. 6,176,848, the contents of which are hereby incorporated by reference as if recited in full herein. While these systems have been used successfully to pump blood, the flow rates provided are typically under 3-4 liters/minute at a counterpressure of about 100 mm Hg. The pumping rate is limited by the low torque limitation of the small "micro" motors.

Indeed, notwithstanding its attractiveness as a less-invasive alternative, most designs for percutaneously-inserted blood pumps exhibit one of more of the following shortcomings: limited pump flow; some degree of hemolysis; and/or require the use of a large catheter/cannular, with a risk of ischemia.

There have been previous attempts, mostly unsuccessful, to increase the flow rate through small diameter catheter blood pumps. Simply increasing the rotation speed of the pump's impeller will increase the flow rate. However, the increased speed results in additional power requirements, which in turn may increase the size and electrical demands of the motor. In devices that use a flexible drive cable to drive the pump's impeller (rather than an in-vivo motor sited near the impeller), the increased motor speed may require an increase in the size and stiffness of the flexible drive cable. Furthermore, the increased speed of the impeller can increase shear stress on the blood, resulting in increased hemolysis.

As mentioned above, catheter blood pumps are usually advanced to the heart through the vascular system. Consequently, there is a limit as to the acceptable diameter of the largest feature of the catheter blood pump. Consider that such a blood pump typically includes various tubes, an impeller housing, an impeller, and a drive cable and/or motor. Since the impeller is rotating at high speed (thousands of rpm), it is important that the impeller does not come into contact with the patient's anatomy or other parts of the blood pump (e.g., tubing, impeller housing, etc.). For a pump having a fixed-diameter, non-foldable/non-expandable impeller, an outermost tube, typically called a sheath, the sheath is typically the largest-diameter feature, whereas other elements of the blood pump (e.g., impeller housing, impeller, etc.) that are intended to be introduced into the vasculature are contained within the sheath. As a consequence, the diameter of the impeller is necessarily smaller than the sheath and smaller than the impeller housing. This typically results in an impeller having a diameter in the range of 9 to 12 Fr, which presents a significant limitation to generating pump flows greater than about 2 liters/minute.

There are several possible operational locations for the catheter blood pump within a patient's vascular system, the most common being placement across the aortic valve, with suction from the left ventricle and discharge into the ascending aorta. Unlike a catheterization procedure, it may be desirable to insert and position the catheter blood pump without the benefit of image-guided procedures via a different technique without requiring an increase in size of the intrabody portions of the catheter blood pump during insertion and placement.

SUMMARY

Embodiments of the invention provide pressure sensors arranged to provide concurrent pressure measurements useful to determine proper placement of the catheter blood pump, in particular the impeller assembly, within the vascular system. In some embodiments, the desired placement is in the ascending aorta. In accordance with the present teachings, proper placement can be determined via measurement of a pressure differential, such as obtained using longitudinally spaced apart fiberoptic pressure sensors.

A pressure differential between pressure measurements provided by the first and second pressure sensors indicates proper positioning (at least when the distal end portion of the catheter blood pump (proximal to the snorkel) is in a linear (unbent) orientation and the pressure differential can be used to identify when the impeller assembly and inlet cage are in the desired respective intracardiac positions, optionally without requiring image-guided procedures.

Embodiments of the invention provide catheter blood pumps with one or more radio-opaque markers that can be used to confirm position of the outlet (impeller) cage and/or intake (suction) cage without requiring fiberoptic pressure sensors or used in combination with the fiberoptic pressure sensors.

Embodiment of the invention are directed to catheter blood pumps that include a housing with inflow and outflow ports and at least one fiberoptic pressure sensor connector, a multi-lumen catheter coupled, at a proximal end thereof, to the housing and also having an inflow liquid flow path coupled to the inflow port and an outflow liquid flow path coupled to the outflow port, and an impeller assembly disposed adjacent to a distal end portion of the multi-lumen catheter. The impeller assembly includes an impeller within an impeller cage, a cannula coupled to a distal end portion of the impeller assembly, an inlet cage provided by or coupled to a distal end portion of the cannula; and first and second fiberoptic pressure sensors. At least a portion of each of the first and second fiberoptic pressure sensors extend longitudinally along and internal to an outer wall of the multi-lumen catheter. The first fiberoptic pressure sensor is longer than the second fiberoptic pressure sensor and has a segment that extends out of a distal end portion of the multi-lumen catheter, along a strut of the impeller cage, then longitudinally along the cannula to terminate proximal to the inlet cage.

The second fiberoptic pressure sensor can terminate proximal to windows of the impeller cage.

The multi-lumen catheter can have a central lumen and one or more peripheral lumens disposed radially outward of the central lumen.

A sensor head of the first fiberoptic pressure sensor can be exposed to environmental conditions via an aperture in an outer wall of the cannula.

The second fiberoptic pressure sensor can terminate inside the multi-lumen catheter.

The second fiberoptic pressure sensor can provide a sensor head proximal to the windows of the impeller cage.

The sensor head of the second fiberoptic pressure sensor can reside a proximal distance in a range of 0.01 inches and 0.25 inches from a proximal end of the windows of the impeller cage.

A sensor head of the second fiberoptic sensor can be exposed to environmental conditions through an aperture in an outer wall of the distal end portion of the multi-lumen catheter.

The one or more peripheral lumens can include a first pressure sensor lumen and a second pressure sensor lumen that is spaced apart from the first pressure sensor lumen. The first fiberoptic pressure sensor can be configured to enter the first pressure sensor lumen via a first entry port in the outer wall of the multi-lumen catheter, distal to a proximal end of the multi-lumen catheter. The second fiberoptic pressure sensor can be configured to enter the second pressure sensor lumen via a second entry port in the outer wall of the multi-lumen catheter, distal to the proximal end of the multi-lumen catheter.

First and second entry ports can reside a distance in a range of 1 mm to 3 inches from the proximal end of the multi-lumen catheter.

The catheter blood pump can further include an adhesive segment coupled to a segment of the first fiber optic sensor and a distal end portion of a lumen of the multi-lumen holding the first fiber optic sensor to provide a fluid barrier.

The catheter blood pump can further include: a first adhesive segment coupled to a sub-length of the first fiberoptic pressure sensor adjacent to the first entry port; and a second adhesive segment coupled to a sub-length of the second fiberoptic pressure sensor adjacent to the second entry port.

The catheter blood pump can include a first adhesive segment coupled to a first portion of the first fiberoptic pressure sensor at an exit location from the multi-lumen catheter and a second adhesive segment longitudinally spaced apart from and proximal to the first adhesive segment, also coupled to the first fiberoptic pressure sensor. The first and second adhesive segments can reside inside a lumen of the multi-lumen catheter holding the first fiberoptic pressure sensor.

The catheter blood pump can further include an adhesive segment proximal to the aperture of the multi-lumen catheter. The sensor head of the second fiberoptic pressure sensor can be free of adhesive and can reside adjacent the aperture of the multi-lumen catheter.

The at least one fiberoptic pressure sensor connector can be provided as a single fiberoptic pressure sensor connector whereby the first and second fiberoptic pressure sensors have proximal ends that are coupled to the single fiberoptic pressure sensor connector.

The segment of the first fiberoptic pressure sensor that extends along the cannula can be sandwiched between an inner wall and outer wall of the cannula.

The housing can be a motor assembly housing that encloses a motor. The catheter blood pump can further include a flexible drive cable operatively coupled, at a proximal end thereof, to the motor, the flexible drive cable can extend from the motor into a central lumen of the multi-lumen catheter. The impeller can be operatively coupled to a distal end portion of the flexible drive cable.

The catheter blood pump can further include a control circuit operatively coupled to the at least one fiberoptic pressure sensor connector and be configured to obtain concurrent pressure measurement signals provided by the first and second fiberoptic pressure sensors.

The control circuit has pressure sensor electronics that communicate with the first and second fiberoptic pressure sensors and the control circuit can be configured to identify correct placement of the inlet cage and impeller cage based on a pressure differential of concurrent pressure measurements from the first and second fiberoptic pressure sensors.

The multi-lumen catheter can have an inflow flush fluid lumen providing at least part of the inflow liquid path and an outflow flush fluid lumen providing at least part of the outflow liquid path. The inflow port can be provided by a flush fluid intake connector that extends outward from the housing and intakes flush fluid from a flush fluid source and the outflow port is provided by a flush fluid waste connector that extends outward from the housing and directs outflow flush fluid to a collection device. The housing can have a flush fluid manifold that is in fluid communication with the flush fluid intake connector, the flush fluid waste connector, the inflow flush fluid lumen, and the outflow flush fluid lumen whereby the manifold is configured to direct flush fluid from the flush fluid intake connector to the inflow flush fluid lumen and direct flush fluid from the outflow flush fluid lumen to the flush fluid waste connector.

The flush fluid intake connector and the flush fluid waste connector can be parallel and can extend at an angle between 30-75 degrees from a sidewall of the housing.

The multi-lumen catheter can have a coaxial arrangement of inflow and outflow flush fluid lumens.

The catheter blood pump can further include a heat shrink outer layer residing distal to the multi-lumen catheter and covering a first segment of the first fiberoptic pressure sensor.

A sensor head of the second fiberoptic pressure sensor can reside in an open channel of a lumen of the multi-lumen catheter and a segment of adhesive can reside proximal to the sensor head in the lumen to define a fluid barrier.

A sensor head of the second fiberoptic pressure sensor can reside proximal to the windows of the impeller cage and the sensor head of the second fiberoptic pressure sensor can have a MOMS structure that is surrounded by an open annular channel free of adhesive.

Other embodiments are directed to a housing assembly for a catheter blood pump. The housing assembly includes: a housing, a flush-fluid inlet connector coupled to the housing and being externally accessible; a flush-fluid outlet connector coupled to the housing and being externally accessible; a power and motor-control signal connector coupled to the housing and being externally accessible; a first fiberoptic pressure sensor connector coupled to the housing and being externally accessible; a second fiberoptic pressure sensor connector coupled to the housing and being externally accessible; and a multi-lumen catheter having a proximal end portion held inside the housing. The multi-lumen catheter comprises inflow and outflow lumens, the inflow lumen in fluid communication with the flush-fluid inlet connector and the outflow lumen in fluid communication with the flush-fluid outlet connector.

The flush-fluid inlet connector and the flush-fluid outlet connector can extend from a common side portion of the housing at an angle from horizontal or vertical that is in a range of 30-75 degrees.

The housing can enclose a motor and the multi-lumen catheter can further include a longitudinally extending center lumen. A drive cable is operatively coupled at a first end thereof to the motor with a proximal end portion of the drive cable held inside the housing. The drive cable extends out of the motor and into the center longitudinally extending lumen.

The multi-lumen catheter can have a coaxial arrangement of inflow and outflow flush fluid lumens. A first fiberoptic sensor resides in the multi-lumen catheter with a portion that extends proximally out of the multi-lumen catheter into the first fiberoptic pressure sensor connector and a second fiberoptic pressure sensor resides in the multi-lumen catheter and has a portion that extends proximally out of the multi-lumen catheter into the second fiberoptic pressure sensor connector.

The multi-lumen catheter can have a plurality of parallel lumens, including a center lumen and circumferentially spaced apart and radially outwardly positioned peripheral lumens. A first fiberoptic pressure sensor can reside in a first of the peripheral lumens with a portion that extends proximally into the first fiberoptic pressure sensor connector and a second fiberoptic pressure sensor can reside in a second of the peripheral lumens with a portion that extends proximally into the second fiberoptic pressure sensor connector.

Still other embodiments are directed to a method of placing a catheter blood pump, optionally without requiring image-guided surgery. The methods include providing a catheter blood pump system with a catheter blood pump having first and second fiberoptic pressures sensors, an inlet cage, and an impeller with an impeller cage. The first and second fiberoptic pressure sensors include sensor heads with a respective MOMS structure held inside a sleeve with an annular open channel free of adhesive. The method further includes: inserting the catheter blood pump intravascularly to place the inlet cage in a first location in a heart of a patient with the impeller cage in a longitudinally spaced apart second location in the heart of the patient; concurrently successively obtaining a first pressure (P1) measurement from the first fiberoptic pressure sensor and a second pressure (P2) measurement from the second fiberoptic pressure sensor during the insertion; monitoring the first and second pressure measurements over time; and electronically identifying a correct placement of the inlet cage and the impeller cage when a defined pressure differential (PD) corresponding to a difference in P1 and P2 occurs.

The first location can be the left ventricle and the second location can be the ascending aorta, and wherein the pressure differential is in a range of 60 mmHg-80 mmHg during diastole of a cardiac cycle.

Further features, advantages and details of the present invention will be appreciated by those of ordinary skill in the art from a reading of the figures and the detailed description of the preferred embodiments that follow, such description being merely illustrative of the present invention.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DETAILED DESCRIPTION

Figure 1:
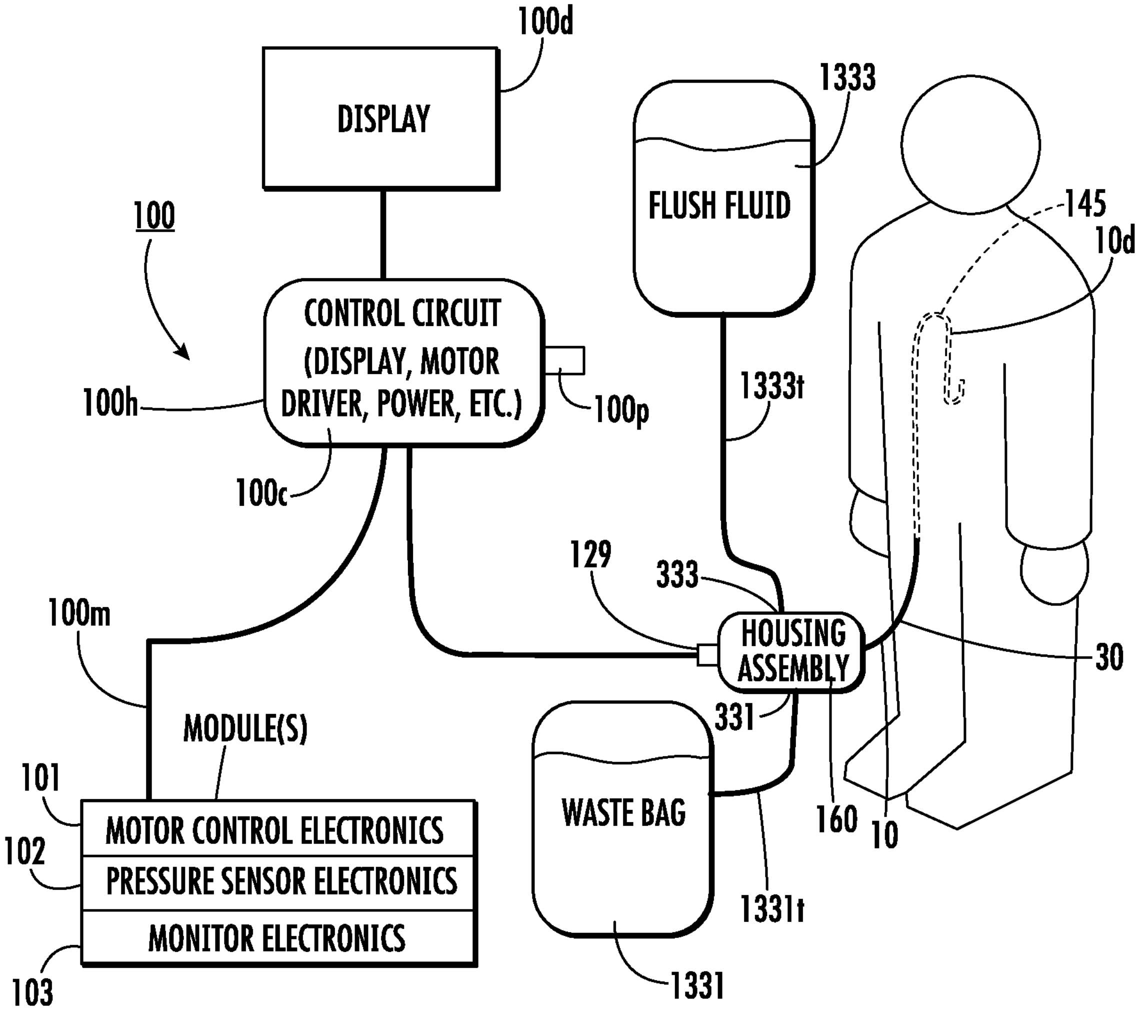
FIG. 1 is a schematic illustration of a catheter blood pump system according to embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. The abbreviation "FIG." may be used interchangeably with "FIG." and the word "Figure" in the specification and figures. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit of flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments. The term "about" means that the noted number can vary by +/−20%.

Generally stated, placement of the catheter blood pump 10 in preparation for use requires advancing the catheter 30 through a tortuous path associated with a patient's vascular system to position the impeller assembly 145 at a desired location, wherein pump suction provided by the inlet cage 33, is distal to the impeller assembly 145 (upstream of the pumped blood flow path whereby pumped blood exits out the cage 44 of the impeller assembly 145), is within the left ventricle of the heart, and the impeller 40 is positioned in the ascending aorta.

Turning now to FIG. 1, an example catheter blood pump system 100 is shown with a control circuit 100*c* and a display 100*d*. The control circuit 100*c* can be provided as a unit with all of the control electronics held in a single housing 100*h*. The unit can also provide the display 100*d* or the display 100*d* may be a separate component. The control circuit 100*c* is in communication with the motor housing assembly 160. In the embodiment shown, the extracorporeal elements of the catheter blood pump system 100 include the control circuit 100*c*, display 100*d*, one or more modules 100*m* with motor control electronics 101, pressure sensor electronics 102 and monitoring electronics 103 as well as the outflow and inflow tubing 1331*t*, 1333*t*, respectively.

The control circuit 100*c* and/or other electronics can be provided in a cloud-based distributed computer system or in a LAN/WAN distributed computer system or may be entirely provided by a processor(s) in the system housing 100*h*.

Figure 2:
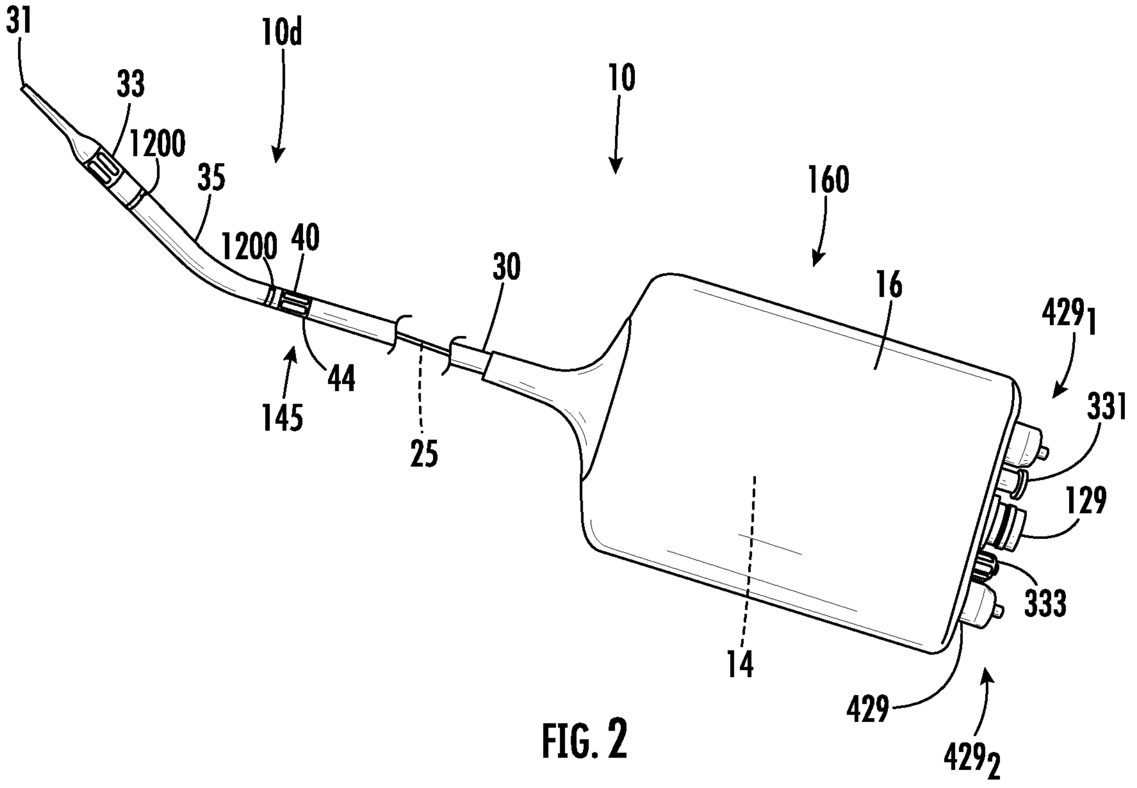
FIG. 2 is a side view of a portion of an example catheter blood pump according to embodiments of the present invention.

Referring to FIG. 2, the housing assembly 160 can contain the motor 14 that drives the pump impeller 40, and also includes various connectors/interfaces such as the power connector 129 and at least one pressure sensor connector 429, shown as two separate pressure sensor connectors 4291, 4292 in FIG. 2. The shaft/catheter 30 may be 4 to 6 feet in length, as it must be long enough to be snaked through the vasculature of an adult (typically the devices are not manufactured to be gender specific) so the length is sufficient to accommodate an adult male, terminating near the heart and starting with an insertion point near the groin into the femoral artery, or at the wrist. However, gender and age specific sizing may be used, e.g., male/female, pediatric versus adult and the like.

FIG. 1 depicts a portion of the catheter 30 with the flexible drive shaft/cable 25 external to the body of the patient, the majority of which resides in a patient's vasculature during use. Flush fluid 1331, as may be contained in an IV bag, is delivered to the blood pump 10 via a connection 333 at the housing assembly 160. A main control circuit 100*c* with at least one digital signal processor of the system 100 can be in communication with and/or include a display 100*d*, a power supply 100*p*, motor controller electronics 101, sensor electronics 102, monitoring electronics 103, and the like. The control circuit 100*c* provides signals and power for the motor 14, which can be contained within the housing 16 of the housing assembly 160 and receives sensor signals from the blood pump 10. Spent flush fluid (outflow fluid) is conveyed to a collection container 1331, shown as waste bag, from the blood pump 10 via an outflow connector 331 coupled to the housing 16 of the housing assembly 160.

Figure 3:
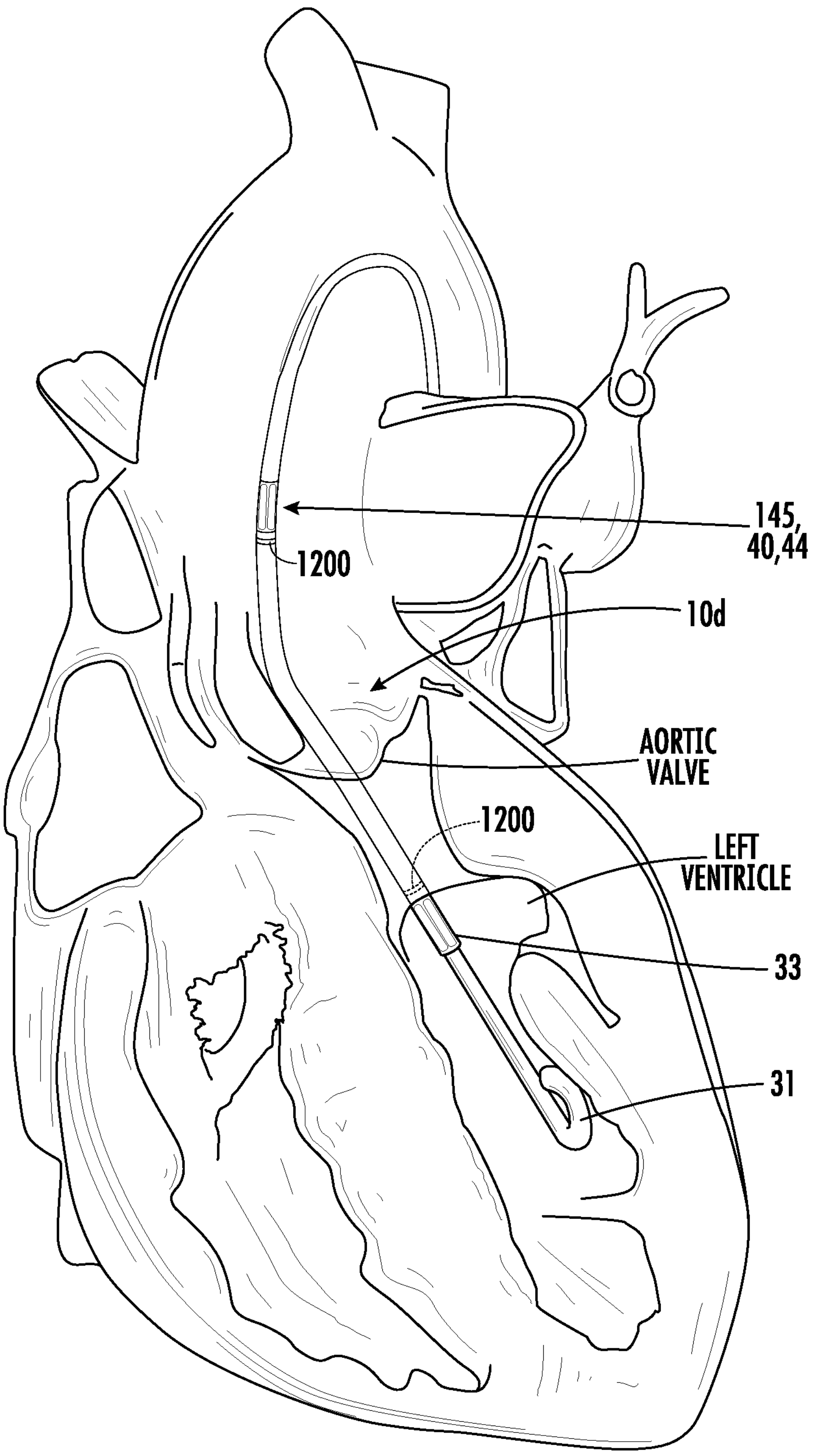
FIG. 3 is a front perspective schematic illustration of a portion of the catheter blood pump in an operative position in the heart according to embodiments of the present invention.
Figure 5:
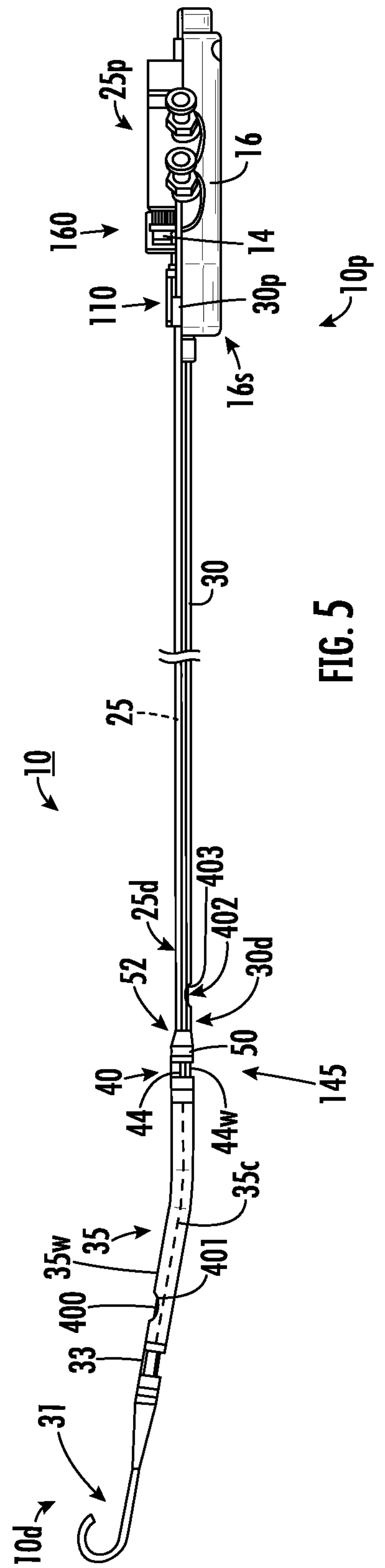
FIG. 5 is another side view of the blood pump shown in FIG. 4, rotated at 90 degrees from the orientation shown in FIG. 4.
Figure 6A:
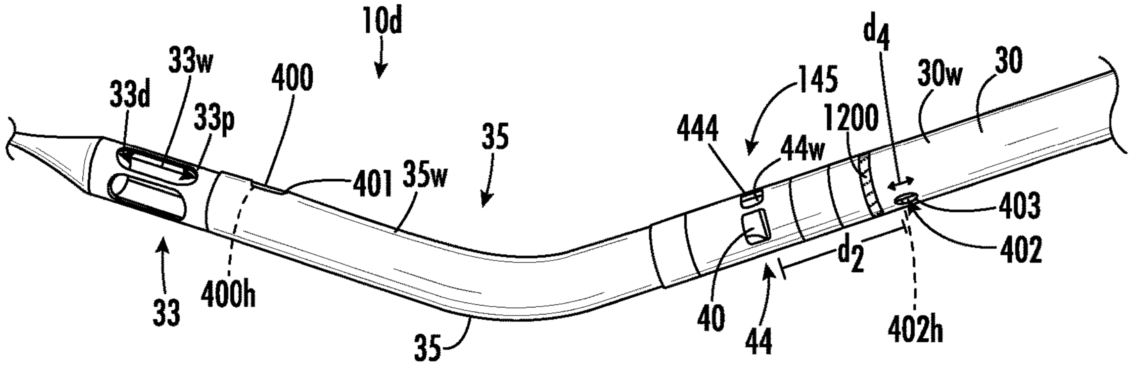
FIG. 6A is a greatly enlarged view of a segment of a distal end portion of another example of a catheter blood pump according to embodiments of the present invention.

FIG. 3 depicts one location for siting the blood pump, wherein the inlet cannula 35 is within the left ventricle, and the impeller assembly 145 is located within the ascending aorta. Proper placement can be determined by measuring pressure on both sides of the aortic valve to obtain a differential pressure. In the illustrative embodiment, pressure is obtained using first and second fiberoptic pressure sensors 400, 402, respectively (FIGS. 5, 6A, for example). Advantages of such sensors 400, 402 include their compact size, and that they are biologically inert and accurate. Moreover, the use of such sensors can avoid measurement pressure losses/dampening, such as if a long narrow lumen were used for remote pressure monitoring.

Referring to FIGS. 2-5, the catheter blood pump 10 comprises the impeller assembly 145 and the (motor) housing assembly 160. The catheter blood pump 10 has a distal end portion 10*d* that provides the impeller assembly 145 and the suction intake or inlet cage 33. The impeller assembly 145 comprises the impeller 40 and the impeller cage 44 with windows 44*w* that defines the pumped blood exit path into the heart. The inlet cage 33 is provided distally to the impeller assembly 145. The inlet (suction) cage 33 can be coupled to a snorkel 31 at a distal end thereof. The inlet cage 33 (proximal end portion) can have or be coupled to a cannula 35. The term "cannula" 35 and can be interchangeably referred to as a "snorkel tube".

A catheter 30 can extend longitudinally out from the housing 16 of the housing assembly 160 to terminate adjacent the impeller assembly 145. In some embodiments, the catheter 30 can enclose the torque cable 25 that connects the motor 14 to the impeller 40 of the impeller assembly 145. Where internal motors are used to rotate the impeller 40, the long drive cable 25 is not required and the external housing assembly 160 can be modified from the embodiments shown to include the power, sensor and fluid connections 331, 333, with the inflow and outflow paths for the purge fluid without requiring the external motor and drive cable.

Generally stated, when the proximal end portion of the torque cable 25 is mechanically rotated by a motor shaft 114 of the motor 14, typically located outside the patient's body, it conveys the rotational force through the length of the multi-lumen shaft 30, causing the impeller 40 to spin at high speed near the heart.

The blood pump 10 can be particularly suitable in providing ventricular assist during surgery or providing temporary bridging support to help a patient survive a crisis.

Referring to FIGS. 4-6C, the catheter 30 has a distal end 30*d* and a proximal end 30*p*. The catheter 30 can be interchangeably referred to as a "multi-lumen shaft" that provides at least part of an inflow path and outflow path of flush fluid 1333 (FIG. 1). The multi-lumen shaft/catheter 30 can provide parallel lumens and/or coaxially arranged lumens. Where an extracorporeal motor is used, a (center) lumen 131 can hold the torque cable 25 and this lumen can be described as a "torque cable lumen." The torque cable lumen 131 can define at least part of a purge liquid out-flow path Fo (shown by arrows in FIG. 6C) that extends to the outflow connector 331.

The motor 14 is arranged to drive the torque cable 25 in the multi-lumen shaft 30 which in turn drives the impeller 40/pump unit. The motor 14, when operated at an extracorporeal site, can have larger sizes relative to internal/intra-body motors. The multi-lumen shaft 30 provides continuous lubrication by a biocompatible (purge) liquid. A part of this liquid can exit through a bearing housing/impeller shaft interface and thus enter the blood stream. The remaining (primary) part can be directed to flow through an out-flow path and be collected extracorporeally after passing through an outflow lumen 131 (FIGS. 7, 8A, 8B) provided in the multi-lumen shaft 30 that also holds the drive cable 25.

Referring to FIGS. 4, 7, 8A and 8B, the multi-lumen shaft 30 can have at least one inflow lumen 133 that can define at least part of a (purge) fluid inflow path Fi, from connector 333 to the manifold 110 then to the inflow lumen(s) 133.

Figure 4:
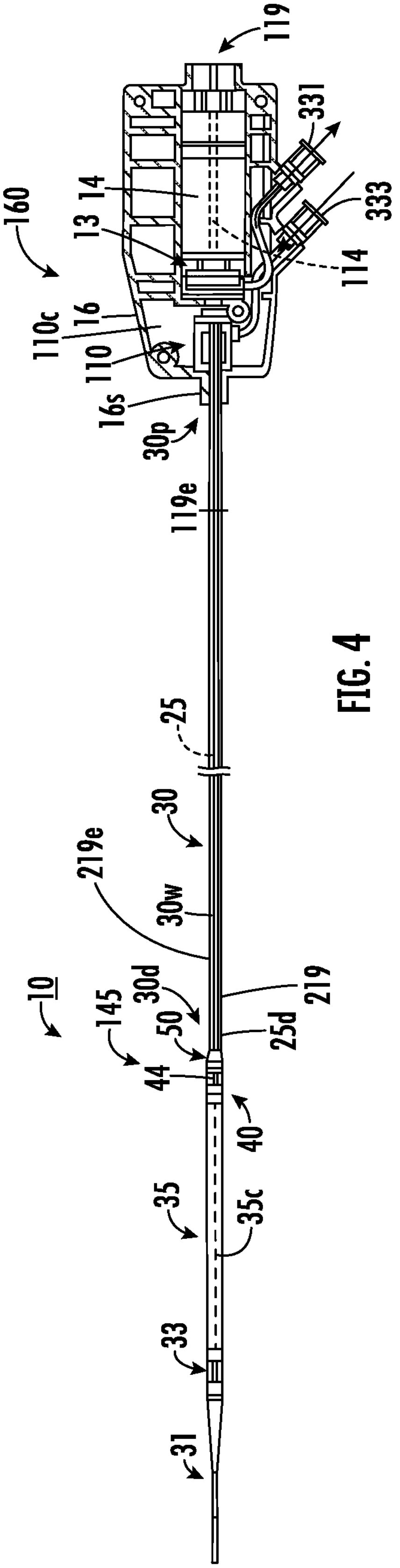
FIG. 4 side view of a blood pump, with one part of a shell handle omitted to reveal internal components, according to embodiments of the present invention.

As shown in FIG. 4, the flush-fluid inlet connector 333, and the flush-fluid outlet connector 331 can extend adjacently and from a common side portion of the housing 16 of the housing assembly 160 at an angle from horizontal that is in a range of 30-75 degrees. This may facilitate ease of assembly to corresponding flow conduits.

Referring to FIGS. 5, 6A-6C, 7, 9A, 9B, 10A and 10B, the catheter blood pump 10 can include first and second fiberoptic sensors 400, 402, respectively, which terminate proximally into at least one fiberoptic pressure sensor connector 429. The at least one fiberoptic pressure sensor connector 429 can be coupled to the housing assembly 160 and configured for conducting signals between the catheter blood pump 10 and the externally located control circuit 100*c* with the sensor electronics 102.

The distal end portion 400*d* of the first pressure sensor 400 has a sensor head 400*h* which may comprise a MOMS (micro-optical mechanical systems) structure coupled to the glass fiber 400*f* of the fiberoptic pressure sensor 400. The distal end portion 402*d* of the second pressure sensor 402 has a sensor head 402*h* which may comprise a MOMS (micro-optical mechanical systems) structure coupled to the glass fiber 402*f* of the second fiberoptic pressure sensor 402.

The fiberoptic pressure sensors 400, 402 can have respective sensor heads 400*h*, 402*h* that are configured with a Fabry-Pérot ("F-P") cavity which comprises two parallel reflecting mirrors on either side of a transparent medium, where the distance between the minors is known as the cavity length. The reflection spectrum of the F-P cavity has distinct peaks in wavelength as a function of the cavity length, physically corresponding to resonances of the cavity. The pressure transducers can be configured to have a flexible embodiment of the F-P cavity. Generally stated, a deformable membrane is assembled over a vacuumed cavity, forming a small drum-like structure. The bottom of the drum and the inner surface of the flexible membrane form the sensing F-P cavity. When pressure is applied, the membrane is deflected towards the bottom of the drum, thus reducing the cavity length. With sensor calibration, the cavity length will correspond to a very precise pressure value. The signal conditioner is designed to be able to accurately determine the cavity length with (nanometer) precision. See, "Medical Pressure Monitoring" brochure provided by FISO Technologies Inc., a leading developer and manufacturer of fiberoptic sensors and signal conditioners, Quebec, Canada, available via the website "FISO.com" as of Jun. 8, 2023, the contents of which are hereby incorporated by reference as if recited in full herein.

The multi-lumen shaft 30 can have an aperture 403 (which may be referred to as a "skyve") in the wall 30*w* to expose a distal end portion 402*d* of the second fiberoptic pressure sensor 402 to local environmental conditions (e.g., blood pressure in the heart). The cannula 35 can have an aperture 401 (which may be referred to as a "skyve") in the (outer) wall 35*w* to expose the distal end portion 400*d* of the first pressure sensor 400 to environmental conditions. However, other placements and configurations of the catheter 30, cannula 35 and/or fiberoptic pressure sensors 400, 402 do not require apertures 401, 403 through the outer wall.

Figure 6B:
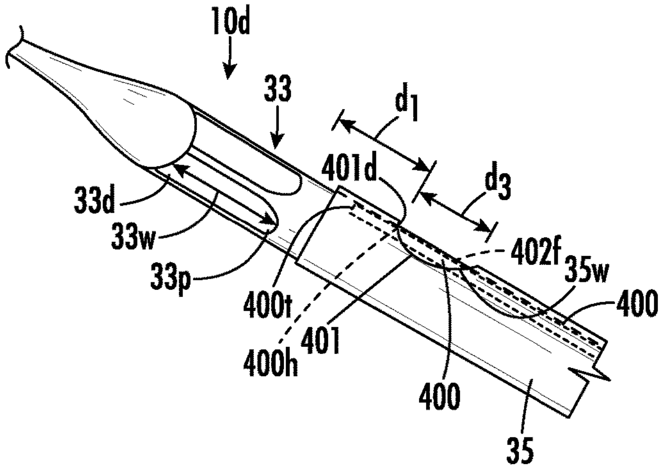
FIG. 6B is a greatly enlarged view of the segment of the distal end portion of the catheter blood pump shown in FIG. 6A, shown rotated and further enlarged relative to the view of FIG. 6A.
Figure 6C:
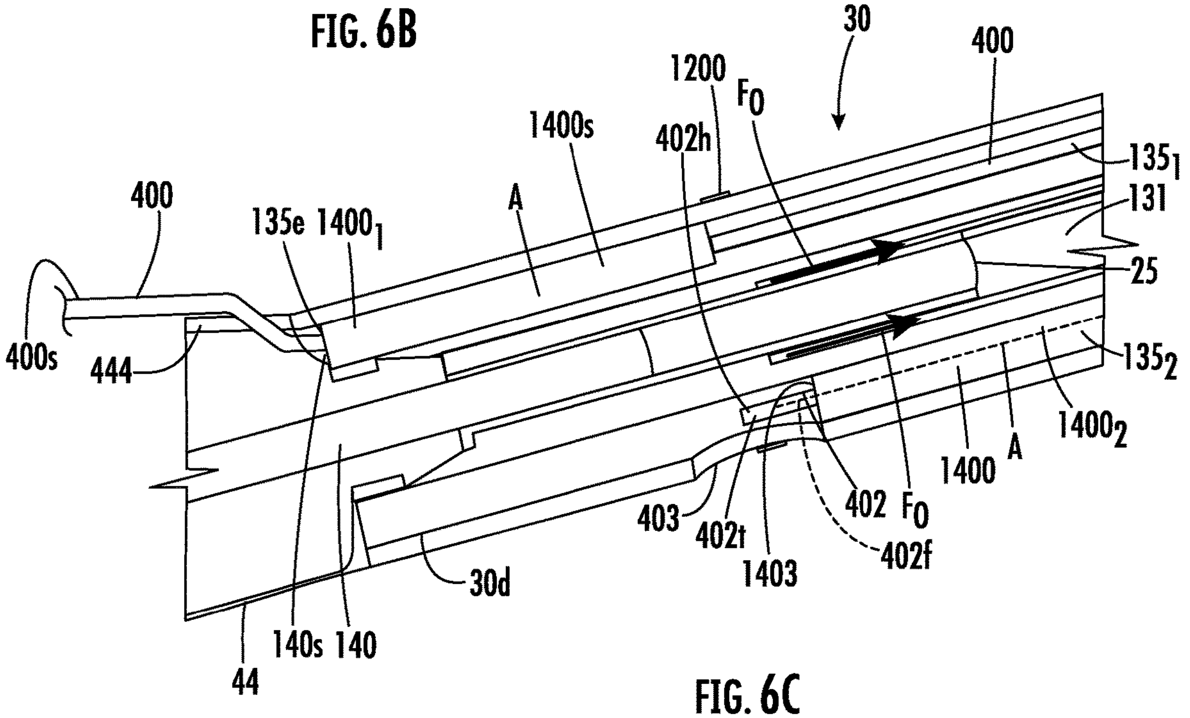
FIG. 6C is a greatly enlarged section view of another segment of the distal end portion of the catheter blood pump shown in FIG. 6A according to embodiments of the present invention.
Figure 6D:
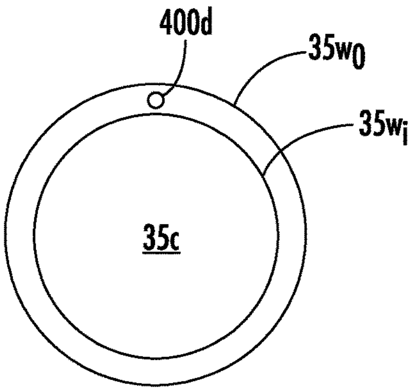
FIG. 6D is a schematic cross-sectional view of a portion of a cannula with a fiberoptic sensor according to embodiments of the present invention.
Figure 6E:
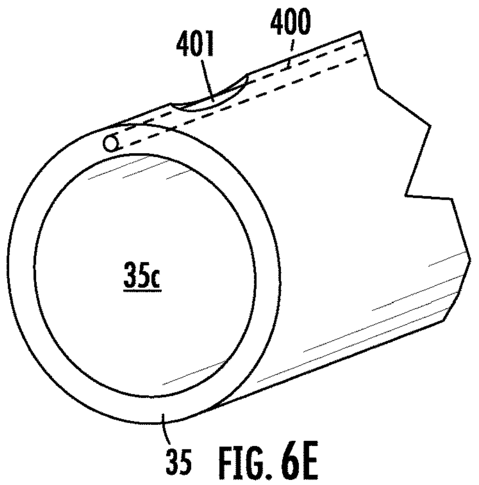
FIG. 6E is a schematic side perspective view of a portion of the cannula shown in FIG. 6D according to embodiments of the present invention.
Figure 6F:
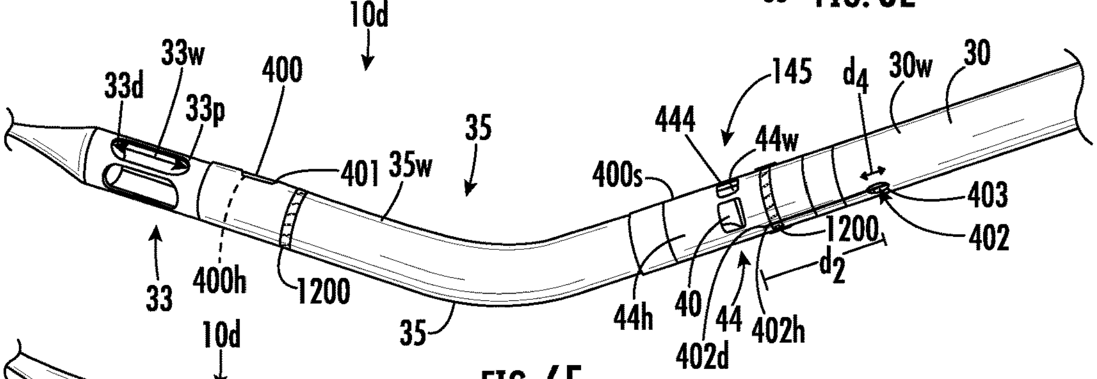
FIG. 6F is a greatly enlarged view of a segment of a distal end portion of another example of a catheter blood pump according to embodiments of the present invention.
Figure 6G:
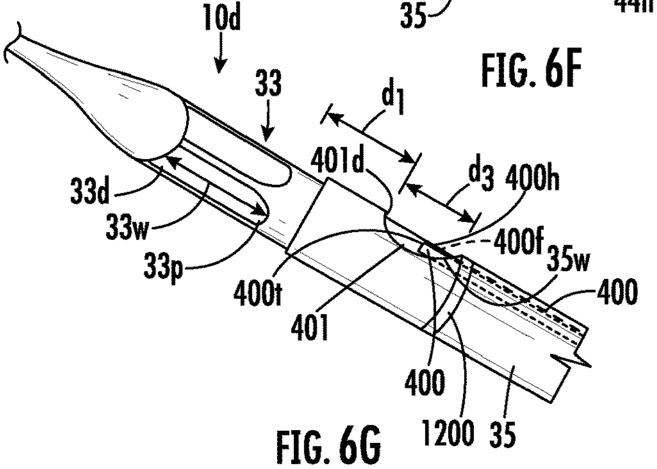
FIG. 6G is a greatly enlarged view of the segment of the distal end portion of the catheter blood pump shown in FIG. 6F, shown rotated and further enlarged relative to the view of FIG. 6F.
Figure 6H:
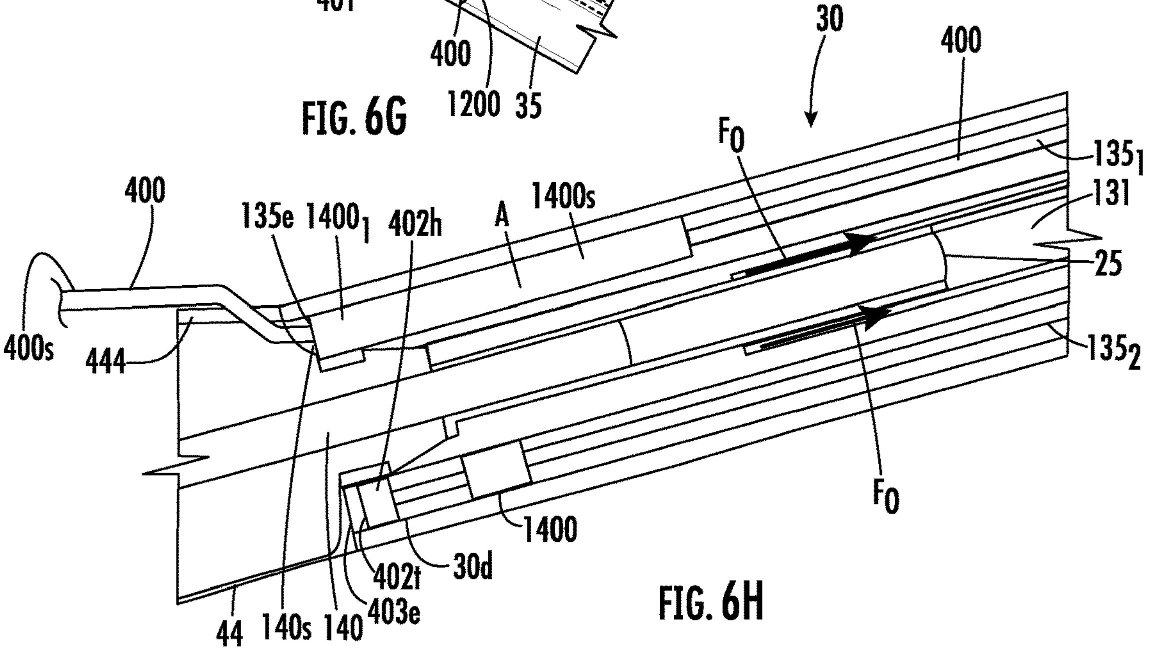
FIG. 6H is a greatly enlarged section view of another segment of the distal end portion of a catheter blood pump according to embodiments of the present invention.
Figure 6I:
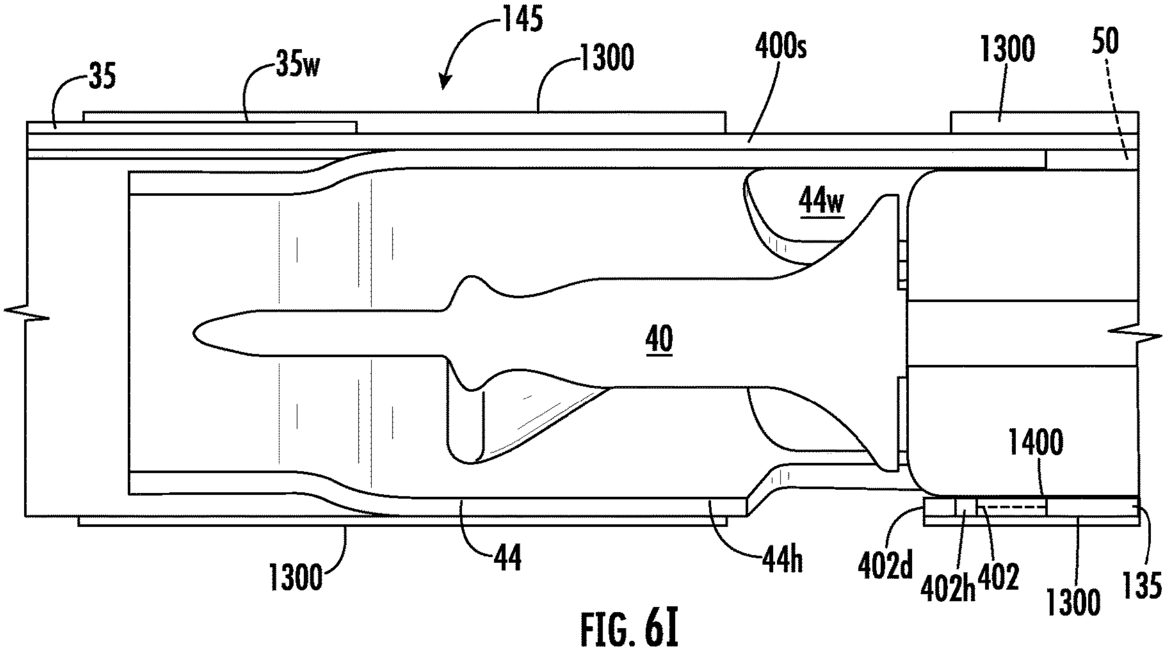
FIG. 6I is a greatly enlarged partial section view of a portion of a catheter blood pump according to embodiments of the present invention.
Figure 6J:
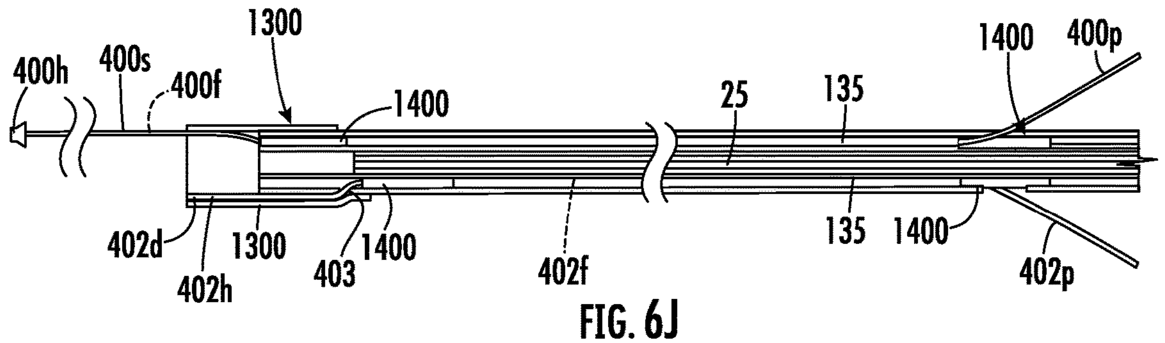
FIG. 6J is a partial section view of a portion of a catheter blood pump showing two fiberoptic pressure sensors according to embodiments of the present invention.
Figure 6K:
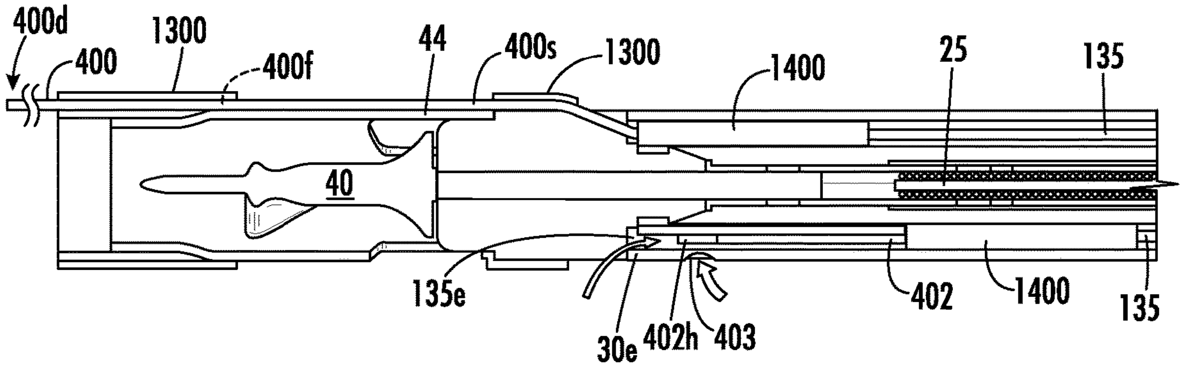
FIG. 6K is a partial section view of a portion of a catheter blood pump showing two fiberoptic pressure sensors according to embodiments of the present invention.
Figure 6L:
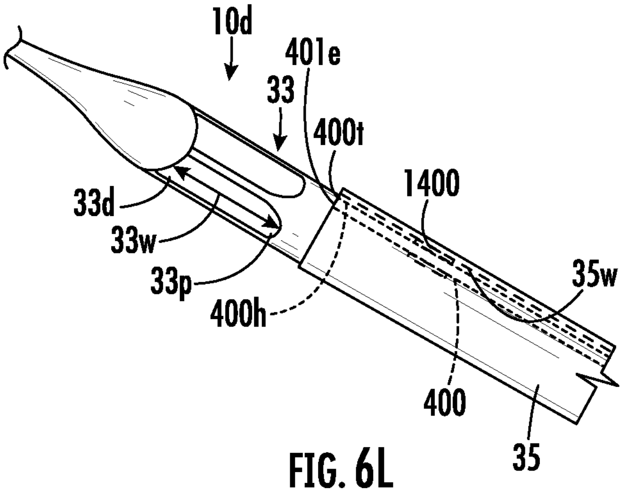
FIG. 6L is a partial section view of a portion of a catheter blood pump showing a distal fiberoptic pressure sensor configuration according to embodiments of the present invention.

For example, the cannula 35 can be configured to hold the fiberoptic pressure sensor 400 so that an open end of a channel 401*e* exposes the sensor head 400*h* in a longitudinal direction to the local environment (FIG. 6L). Adhesive or epoxy 1400 can seal the end channel aperture 401*e* adjacent and proximal to the sensor head 402*h* to inhibit blood flow upstream thereof.

Referring to FIG. 6H, in some embodiments, the proximal second fiberoptic pressure sensor 402, the catheter 30 can be configured so that the lumen 135 holding the second fiberoptic pressure sensor 402 is open at a distal end portion providing an end opening 403*e* that exposes the sensor head 402*h* to local conditions in a longitudinal direction (FIG. 6H). Adhesive, expoxy or other sealant 1400 can be provided in the lumen 135 adjacent to but proximal to the sensor head 402*h*.

In other embodiments, referring to FIGS. 6F, 6J, the second (proximal) fiberoptic sensor 402 can be configured so that a distal end portion 402*d* is routed out an aperture 403 in the wall 30*w* to position the fiberoptic sensor head 402*h* adjacent a proximal end of the impeller cage 44, proximal to the cage windows 44*w*. An adhesive such as cyanoacrylate and/or heat shrink sleeve (tube) overlayer 1300 can be used to hold the distal end portion 402*d* of the second fiberoptic pressure sensor 402 in position. The sensor head 402*h* with the MOMS structure 1020 can be held inside the sleeve 1035 of the fiber optic sensor 402 and can be configured to be able to move independent of/relative to the cage housing 44*h*, e.g., a tight interface against the surface of the cage housing 44*h* is not required. The sensor head 402*h* can be configured so that local pressure is measured using the MOMS structure 1020 and the sensor head 402*h* can be loosely connected to the impeller housing or reside proximal to the impeller housing, in the catheter body 30*b*.

At least part of the distal end portion 400*d* of the first fiberoptic sensor 400 and at least part of the distal end portion 402*d* of the second fiberoptic sensor 402 can be fluidically exposed to contact local fluid (e.g., blood) in the local environment and therefore, be fluidically exposed to blood pressures at the sensor heads 400*h*, 402*h*.

Figure 7:
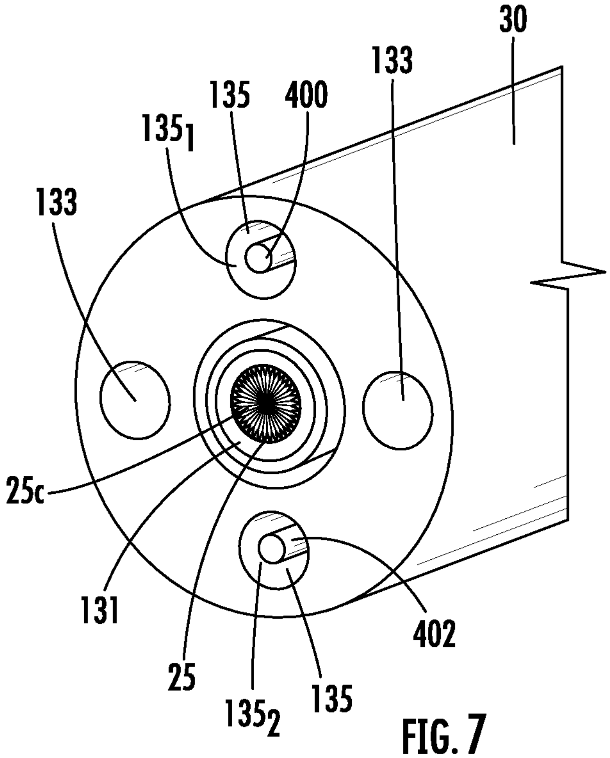
FIG. 7 is a greatly enlarged end view of a multi-lumen shaft/catheter shown in FIG. 6A according to embodiments of the present invention.

The fiberoptic sensors 400, 402 can extend in a straight linear orientation inside a shared lumen 135 or be held in separate lumens 135 of the multi-lumen shaft 30. As shown in FIG. 7, the first and second fiberoptic sensors 400, 402 are held spaced apart, typically parallel, in respective longitudinally extending lumens 135 of the multi-lumen shaft 30. The first fiberoptic sensor 400 can have a longer length than the second fiberoptic sensor 402 and can have a segment 400*s* that exits the distal end portion 30*d* of the multi-lumen shaft 30, travels along a strut 444 of the impeller cage 44 distally, to terminate at a position that is proximal to the inlet cage 33.

Referring to FIGS. 6A, 6B and 6C, the segment 400*s* of the first fiberoptic sensor 400 that is distal to the multi-lumen shaft 30 can be routed against the strut 444, held against, optionally affixed to an outer surface of the strut 444. A heat shrink sleeve 1300 (FIGS. 6I, 6J) can be applied to hold a segment of the fiber optic sensor 400*s* against a sub-length/segment of the fiberoptic pressure sensor 400 about a portion of the impeller cage 44. Alternatively, or additionally, a suitable adhesive or epoxy such as cyanoacrylate may be used to attach a sub-length of the fiberoptic pressure sensor 400 to the cannula 35 and/or impeller (outlet) cage 44.

Referring to FIGS. 6A and 6B, the distal end 401*d* of the aperture 401 for the first fiberoptic sensor 400 can terminate a distance "d1" from a location of a proximal end 33*p* of the inlet cage window 33*w*. The first fiberoptic sensor 400 can be exposed to blood via aperture 401. The distance d1 can be adjacent and proximal to the inlet/suction intake cage 33 to confirm the operative position of the inlet/suction cage 33 is in a left ventricle using the distal sensor 400 during placement and/or operation, e.g., in the left ventricle. In some embodiments, the distance d1 can be in a range of about 0.01 inches to about 2.0 inches. The sensor head 400*h* can reside upstream, downstream or aligned (FIG. 6G) to extend at least partially within the aperture 401. The sensor head 400*h* can reside a short distance from the aperture 401, such as a distance in a range of 0.01 inches and 1 inch. In operative position, in some embodiments, the sensor head 400*h* is in the left ventricle, in fluid communication with the blood/blood pressure in the heart.

Figure 13:
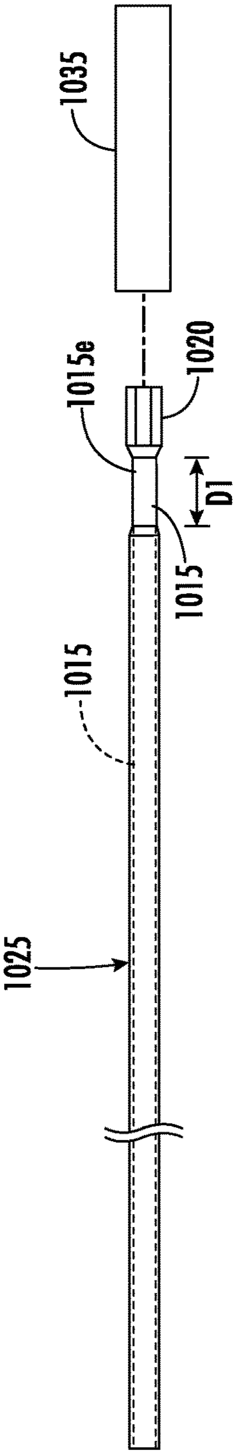
FIG. 13 is an enlarged view of a distal end portion of the fiberoptic pressure sensor shown in FIG. 12 with an end tube separate from the fiberoptic fiber and MOMS unit according to embodiments of the present invention.
Figure 14:
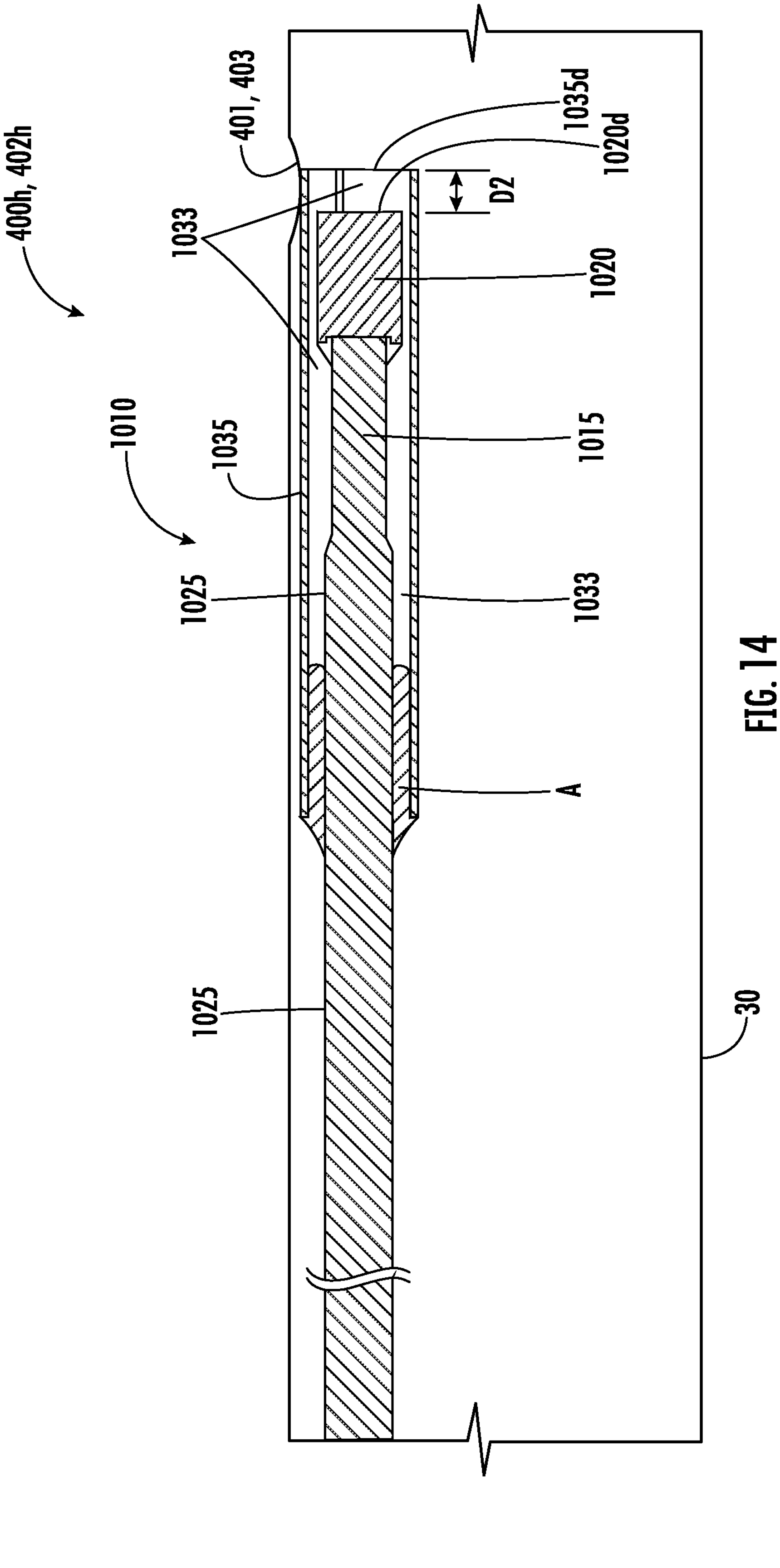
FIG. 14 is a section view of the distal end portion of the fiberoptic pressure shown in FIG. 13 with the end tube assembled to the fiberoptic pressure sensor.

A short length of exposed glass fiber 400*f* can reside upstream of the MOMS structure 1020 (FIGS. 13, 14). Here, the term "exposed glass fiber" means the glass fiber is devoid of an outer jacket or coating but inside the lumen 135 and/or a sleeve 1035 (FIG. 14) at the distal end portion 400*d* of the fiberoptic pressure sensor 400. The length can be about the same as the length (in a longitudinal direction) of the MOMS structure 1020, typically about +/−20% of the length of the MOMS structure 1020.

Referring to FIGS. 6D and 6E, the portion of the first fiberoptic sensor 400 that extends through the cannula 35 can be sandwiched between an inner wall 35*wi* and an outer wall 35*wo*. Sandwiching a major portion of a length of the fiberoptic sensor 400 in heat-shrink wrap 1300 or sandwiching between layers of the body of the cannula 35 can prevent inadvertent detachment from the catheter blood pump 10 compared to when the fiberoptic sensor segment is held against an outer wall with only adhesive or epoxy.

In some embodiments, the first fiberoptic sensor 400 can be routed externally, along an outer wall of the housing 44*h* of the impeller cage 44 and held in position with an adhesive and/or outer heat shrink layer 1300, then routed internally into the cannula 35 (FIG. 6I). Another segment of adhesive and/or heat shrink layer 1300 can reside adjacent but proximal to and longitudinally spaced apart (proximal to the cage windows 44*w* toward the bearing housing 50 (FIG. 4)) from the heat shrink layer 1300 positioned about the cage housing 44*h*. The adhesive can comprise cyanoacrylate or other biocompatible/non-cytotoxic adhesive.

Still referring to FIG. 6I, in some embodiments, the distal end 402*d* of the second fiberoptic sensor 402 can extend distal of the catheter body 30 to terminate proximal to the cage windows 44*w* and can be held in place using the adhesive and/or heat shrink layer 1300 also holding a segment of the first fiberoptic pressure sensor 400.

In some embodiments, the first fiberoptic sensor 400 can have a segment that is routed externally, along an outer wall of the cannula 35 and held in position with an outer heat shrink layer 1300 (FIG. 6K). A longitudinally extending recess can be provided in the outer surface of the cannula 35 to hold a portion or all of the fiberoptic pressure sensor 400 extending along the outer surface of the cannula 35.

FIG. 6K also illustrates that the sensor head 402*h* can be positioned adjacent a distal end 30*e* of the catheter 30. The sensor head 402*h* can be exposed to local pressures via the open end 135*e* of the lumen 135 and/or the aperture/skyve 403.

In some embodiments, a segment of the first fiberoptic sensor 400 can be sandwiched between wall layers of the cannula 35 and another segment of the fiberoptic sensor 400 can reside externally along a portion of the outer wall 35*wo*.

The second fiberoptic sensor 402 can terminate a distance "d2" from a location of a proximal start 44*p* of the window 44*w*. The distance d2 can be adjacent but proximal to the impeller/outlet cage 44, to confirm that the impeller/outlet cage 44 is in the aorta using the proximal sensor 402. Thus, d1 can be selected so that the distal pressure sensor 400 is adjacent but proximal to the inlet cage 33 and the distance d2 can be selected so that the sensor head 402*h* of the proximal pressure sensor 402 is adjacent but proximal to the impeller/outlet cage 44 so that the correct position of the catheter 10 can be determined using pressure measurements/readings from the first and second fiber optic pressure sensors 400, 402. The distance d2 can be in a range of 0.01 inches and 1 inch, in some embodiments.

In preferred embodiments, the distal end portion 402*d* of the second pressure sensor 402 is within 0.01 inches and 0.25 inches proximal to the proximal end of the impeller cage 44 and/or proximal end of the window 44*w*. The distal end portion 402*d* can be proximal to the proximal end of the impeller cage 44 and/or proximal end of the window 44*w* a distance under 0.01 inches, such as, for example, 0.015 inches, 0.020 inches, 0.025 inches, 0.030 inches, 0.035 inches, 0.040 inches, 0.045 inches, 0.05 inches, 0.06 inches, 0.065 inches, 0.07 inches, 0.075 inches, 0.080 inches, 0.085 inches, 0.09 inches, 0.095 inches and 0.1 inches. The distance of the sensor head 402*h* from the proximal end of the window 44*w* can correspond to a normal or minimal thickness of the aortic valve so that the pressure readings from the second fiberoptic pressure sensor 402 reflect proper position of the cage 44 in the aorta.

Referring to FIG. 6A, in some embodiments, the sensor head 402*h* of the second fiber optic pressure sensor 402 and a radio-opaque marker 1200 can both reside a short distance proximal to the outlet/impeller cage 44. Cardiologists can perform the insertion of the catheter 10 and proper placement can be based on a defined spacing of the radio-opaque marker 1200, e.g., based on predefined information regarding the distance of the radio-opaque marker 1200 from the outlet cage 44, and the catheter position can be adjusted accordingly. For example, the marker 1200 and the sensor head 402*h* can be about 1 cm (maximal) proximal to the outlet cage 44 and cardiologists can then be informed that when using the catheter blood pump system 100, the pressure reading from the second fiber optic pressure sensor 402 is based on that defined position of 1 cm (maximal) that is proximal to the outlet cage 44.

In some embodiments, the marker 1200 can extend circumferentially (over) aligned with at least a portion of the sensor head 402*h* (FIG. 6C). In some embodiments, the marker 1200 can be within 1 cm of and distal to the sensor head 402*h* (FIG. 6A). In some embodiments, the marker 1200 can be within 1 cm of and proximal to the sensor head 402*h* of the second fiber optic pressure sensor (FIG. 6G). In some embodiments, the sensor head 402*h* of the second fiber optic pressure sensor 402 can be proximal to the marker 1200 and the impeller 40 while the marker 1200 can be distal to at least a portion of the impeller 40, distal to the cage windows 44*w* (FIG. 6F).

FIGS. 2 and 3 show two longitudinally spaced apart radio-opaque markers 1200, one adjacent the intake cage 33 and one adjacent the impeller (outlet) cage 44. In some embodiments, the radio-opaque marker 1200 adjacent the impeller cage 44 is distal to the windows 44*w* of the cage 44. It is also contemplated that, on some embodiments, the radio-opaque markers 1200 can be used to confirm positions of each cage 33, 44 without requiring the fiberoptic pressure sensors 400, 402. Different patterns and/or shapes can be used to form the different radio-opaque markers 1200 for visual indicia of distinction from each other.

A short length of exposed glass fiber 402*f* can be upstream of the MOMS structure (1020, FIG. 13, 14) at the distal end portion 402*d* of the fiberoptic pressure sensor 402. Here, the term "exposed glass fiber" means the glass fiber is devoid of an outer jacket or coating but inside the lumen 135 and/or a sleeve 1035 (FIG. 14). The length can be about the same as the length (in a longitudinal direction) of the MOMS structure 1020, typically about +/−20% of the length of the MOMS structure 1020.

The sensor head 402*h* can reside a short distance upstream, a short distance downstream or aligned to extend at least partially within the aperture 403. The term "short distance" for the sensor head 402*h* refers to a distance measured from the tip 402*t* to the adjacent aperture position that is in a range of 0.01-1 inch.

The aperture 401 can have a longitudinal length d3 and the aperture 403 can have a longitudinal length d4 with d3 and d4 being less than a length of the adjacent inlet or impeller cage window 33*w*, 44*w*, respectively. In some embodiments, d3>d4. In some embodiments, d3=d4. In some embodiments, d3<d4. In some embodiments, each aperture 401, 403 can be elongate, with a length dimension greater than a circumferential dimension.

FIG. 6B shows that the first optical fiber pressure sensor 400 can have a tip segment 400*t* that terminates proximal to the cage window 33*w* and distal to the aperture 401. This tip segment 400*t* can be bonded, sandwiched between extruded layers, or otherwise coupled to the cannula 35 to hold the fiberoptic sensor 400 in a desired operational orientation with respect to the aperture 401. FIG. 6A depicts the regions of the catheter blood pump near to, and on either side of the impeller assembly 145. The location of the sensor head 400*h* of the first fiberoptic pressure sensor 400 is proximal to the inlet cage 33 (suction pump intake) of the cannula 35 but distal to the impeller cage 44, and the location of the second fiberoptic pressure sensor 402 is adjacent to the impeller assembly 145. In some embodiments, the second fiberoptic pressure sensor 402 positions the sensor head 402*h* within 0.25 inches proximal to a window 44*w* of the impeller cage 44. When the catheter blood pump 10 is positioned as depicted in FIG. 3, these pressure sensor locations will provide pressure measurements in the left ventricle and the ascending aorta.

FIGS. 6B and 6C depict enlarged representations of these regions, showing the example apertures 401, 403 in each of the cannula 35 and catheter 30, respectively, at which the sensor heads 400*h*, 402*h* of the corresponding fiberoptic pressure sensors 400, 402, respectively, are exposed to the ambient environment (i.e., the blood/blood pressures in the heart during a cardiac cycle).

Figure 10A:
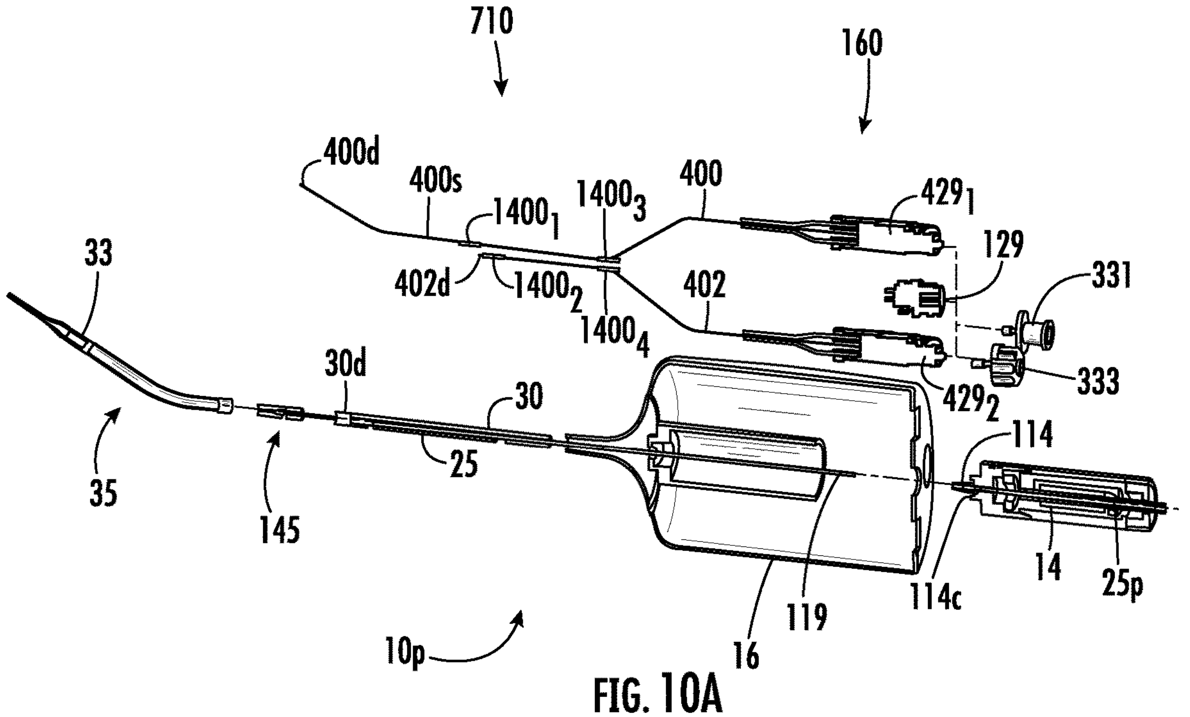
FIG. 10A is a partially exploded view of components of a catheter blood pump according to embodiments of the present invention.
Figure 10B:
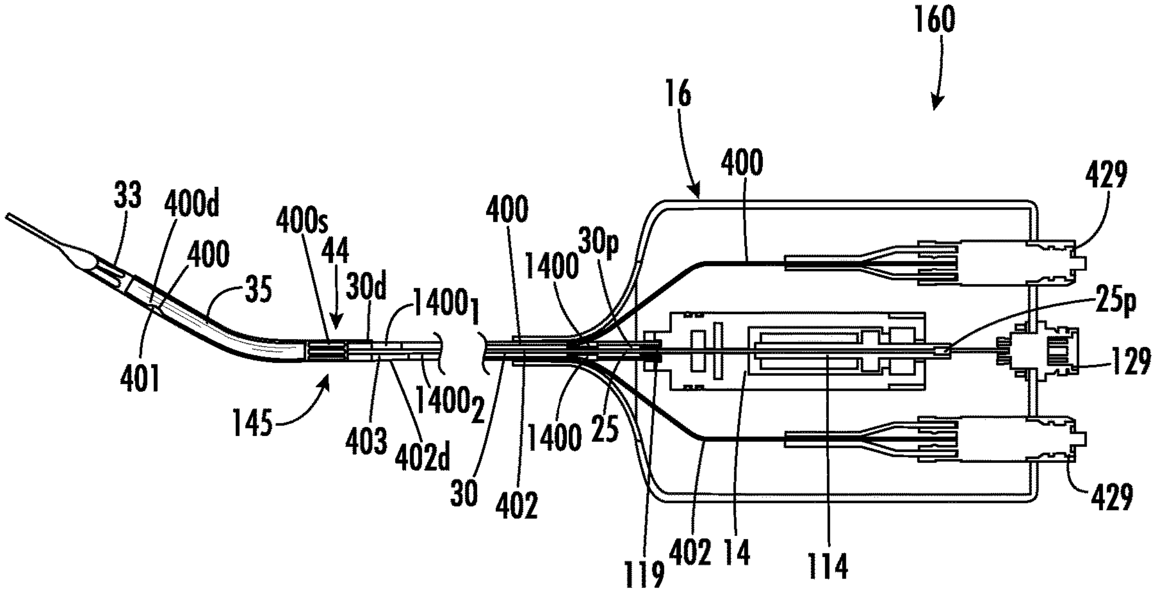
FIG. 10B is a partial section, assembled view of the catheter blood pump and components shown in FIG. 10A.

Turning now to FIGS. 6C, 10A and 10B, the catheter blood pump 10 can also comprise a plurality of adhesive segments 1400, at least one at a defined location for each of the first and second fiberoptic pressure sensors 400, 402, respectively. The adhesive segments 1400 can have a relatively short length, e.g., a sub-length, such as about 0.5% to about 30% of an overall length of a respective fiberoptic pressure sensor 400, 402. The adhesive segments 1400 can have a relatively short length that is in a range of 0.1 inches to about 2 inches, in some embodiments. Different adhesive segments can have different lengths. These adhesive segments 1400 can define a fluid barrier and inhibit blood from traveling proximal thereto.

The adhesive segments 1400 can be provided as first and second longitudinally spaced apart adhesive segments for each of the first and second fiberoptic pressure sensors 400, 402, respectively. The adhesive segments 1400 can have the same or different adhesives and/or epoxies and the adhesive segments can be flexible when cured and may be flowably applied. The adhesive(s) providing the adhesive segments 1400 can be a biocompatible and/or non-cytotoxic adhesive A. To be clear, the term "adhesive" is used broadly to encompass epoxies and other materials that can provide the fluid barrier and attachments to local catheter structure.

As shown in FIG. 6C, a first adhesive segment $\mathbf{400}_1$ can reside in a first lumen $\mathbf{135}_1$ and a second adhesive segment $\mathbf{400}_2$ can reside in a second lumen $\mathbf{135}_2$ of the multi-lumen shaft 30 at a distal end portion 30*d* of the multi-lumen shaft 30. The first fiberoptic pressure sensor 400 can extend distal to the first adhesive segment $\mathbf{1400}_1$ and out of the distal end portion 30*d* of the multi-lumen catheter 30 to extend along the strut 444 of the impeller cage 44.

The second adhesive segment $\mathbf{1400}_2$ can terminate adjacent the aperture 403. A tip end portion 402*t* of the second fiberoptic pressure sensor 402 can extend distally of the adhesive segment $\mathbf{1400}_2$ to align with the aperture 403.

In some embodiments, the adhesive segments 1400 can be provided using sleeves 1400*s* that can be affixed to a segment(s) of the respective lumens 135. The adhesive A of the adhesive segments 1400 can extend externally about the sleeve 1400*s* as well as internally to affix or secure the respective optical fiber pressure sensor segment of the optical fiber pressure sensor 400 or 402 thereat. An epoxy, adhesive or other sealant 1403 can reside/be injected or otherwise positioned inside the sleeve 1400*s*, between an outer wall of the fiberoptic pressure sensor 400 or 402, and an inner wall of the sleeve 1400*s* (and the space, if any, between the sleeve 1400*s* and the respective lumen 135) to define a fluid barrier and inhibit blood from entering the sleeve 1400*s* and from flowing toward the housing assembly 160.

FIGS. 10A and 10B illustrate that the adhesive segments 1400 can be provided as a first and second adhesive segments $\mathbf{1400}_1$, $\mathbf{1400}_3$ in the first lumen $\mathbf{135}_1$ and a first and second adhesive segment $\mathbf{1400}_2$, $\mathbf{1400}_4$ in the second lumen $\mathbf{135}_2$, one at or adjacent an entry port 135*i* formed through the outer wall 30*w* of the multi-lumen shaft 30 (catheter) and into an adjacent lumen 135. For the first fiberoptic pressure sensor 400, one adhesive segment $\mathbf{1400}_1$ can be at or adjacent an exit port 135*e* of the first lumen $\mathbf{135}_1$. For the second lumen $\mathbf{135}_2$, the first adhesive segment $\mathbf{1400}_2$ is adjacent the aperture 403, leaving the fiberoptic pressure sensor portion at the aperture 403, free of adhesive and exposed at the aperture 403 (FIG. 6C), longitudinally spaced apart from the entry port 135*i* and adhesive segment $\mathbf{1400}_4$. The entry ports 135*i* through the outer wall 30*w* of the multi-lumen shaft 30 (catheter) can be circumferentially spaced apart and diametrically opposing each other. In other embodiments, one entry port 135*i* can be offset longitudinally from the other (not shown).

The adhesive segments $\mathbf{1400}_3$, $\mathbf{1400}_4$, that are adjacent the respective entry ports 135*i* can reside inside the multi-lumen catheter 30 and inside the housing 16 as shown in FIG. 10B. These adhesive segments $\mathbf{1400}_3$, $\mathbf{1400}_4$ can provide increased stiffness and/or strain support for the fiberoptic pressure sensors 400, 402.

The entry port(s) 135*i* for the fiberoptic pressure sensors 400, 402 can reside inside the housing 16 (FIG. 10B). The entry port(s) 135*i* can reside a longitudinal distance "D" from the proximal end 30*p* of the multi-lumen catheter 30 that is in a range of 1 mm and 3 inches, in some embodiments.

Where used, the sleeves 1400*s* can facilitate routing, assembly of the fiberoptic sensors 400, 402, provide a fluid barrier and/or a strain relief/support for the respective fiberoptic pressure sensors 400, 402.

Referring again to FIGS. 4 and 5, the blood pump 10 can also have a bearing housing 50 adjacent the impeller 40 with a bearing housing adapter 52 that couples an outer wall 30*w* of the multi-lumen shaft 30 to the bearing housing 50. The bearing housing 50 can comprise a lateral cross-flow passage that is in fluid communication with a radially extending passage of a bearing/bushing and a longitudinal channel thereof, and that provides part of the out-flow path Fo.

Referring to FIGS. 4, 8A, 8B, 10A and 10B, the blood pump 10 can comprise a (first) support wire 119 that resides inside a least a longitudinally extending segment of a center channel 25*c* (FIG. 7) of the torque cable 25. Referring to FIG. 4, the support wire 119 can have a distal end 119*e* that terminates a range of 1-3 inches from a manifold 110 of the housing assembly 160 and that extends at least partially through a center channel 114*c* of the motor shaft 114, shown as extending entirely through the motor shaft 114 in FIG. 4.

As shown in FIG. 4, in some embodiments, the multi-lumen shaft 30 can also include a second support wire 219 that is longitudinally spaced apart from the first support wire 119 and that can reside inside the channel of the torque cable 25. The second support wire 219 can have a proximal end 219*e* that terminates a range of 1-3 inches from the proximal end of the impeller shaft 140. The first support wire 119 can support the torque cable 25 at a high torque area (at the motor 14) so that the torque cable 25 does not collapse under load. The first support wire 119 can also act as a strain relief when it exits a distal end of the manifold 110. The second support wire 219 can allow the impeller shaft 140 and torque cable 25 to be crimped together by using a proximal bushing without collapsing the (hollow) torque cable 25. The second support wire 219 can also act as a strain relief.

In some embodiments, the first and second support wires 119, 219 can be provided as a single support wire instead of separate support wires and the single support wire may extend substantially an entire length of the torque cable 25 or reside only at a proximal end portion or only at a distal end portion of the torque cable 25. In some embodiments, no support wire(s) are required.

Referring to FIGS. 4 and 5, the housing assembly 160 can have a manifold 110 that is coupled to the motor 14. The manifold 110 has a manifold chamber 110*c*. The manifold 110 can sealably enclose a sub-length of the shaft 30, typically at least a segment of the proximal end portion 30*p* of the multi-lumen shaft 30 and can define at least a portion of a (purge) fluid in-flow path of the multi-lumen shaft 30, then into at least one in-flow lumen(s) 133 provided by the multi-lumen shaft 30. The term "in-flow" can be used interchangeably with the term "inflow" herein. The term "out-flow" can be used interchangeably with the term "outflow" herein.

The motor housing 16 can be provided as a cooperating pair of handle shells 16*s*. The motor housing 16 can be an extracorporeal housing.

Turning again to FIGS. 10A and 10B, a partial section view of the proximal end portion of the blood pump 10 is shown. As shown, the motor 14 has a motor shaft 114 that can have a through channel 114*c* that holds a proximal portion 25*p* of the torque cable 25. The torque cable 25 can extend distally out of the channel 114*c* of the motor shaft 114 into a lumen 131 of the multi-lumen shaft 30. The torque cable 25 can be bonded to the inner wall 114*w* of the channel 114*c*. The torque cable 25 can extend through at least 50% of an axially extending length of the channel 114*c*. The torque cable 25 can extend entirely through the channel 114*c* with a greater length in a distal direction outside the motor 14 facing the impeller 40 than in a proximal direction outside the motor 14. The motor shaft 114 can be metal and may have a diamond like coating (DLC) on an inner and/or outer surface thereof to provide hardness, improved surface finish and lubricity. The outer diameter of the motor shaft 114 is preferred to be as small as possible to reduce the surface speed which improves the lifespan of the seal. In some embodiments, the surface speed is about 773 ft/min when the motor shaft 114 is rotating at about 50,000 rpm. The maximal outer diameter of the motor shaft 114 over at least a major portion of its length (50% or greater) can be in a range of 0.0100 inches to 0.050 inches, such as about 0.060 inches.

The catheter/multi-lumen shaft 30 can have a proximal end portion 30*p* that is adjacent the motor 14 and an opposing distal end portion 30*d* that terminates adjacent the impeller 40. The torque cable 25 also has a proximal end portion 25*p* that is coupled to the motor 14 and an opposing distal end portion 25*d* that terminates adjacent the impeller 40. The torque cable 25 can also be interchangeably referred to as a "drive cable". The torque cable 25 can be directly or indirectly attached to the impeller 40 at the distal end portion 25*d* of the torque (drive) cable 25 and to the motor 14 at the proximal end portion 25*p* of the torque (drive) cable 25.

Further discussion of example components of a catheter blood pump according to some embodiments of the present invention can be found in co-pending PCT/US2023/021351, filed May 8, 2023, the contents of which are hereby incorporated by reference as if recited in full herein.

The multi-lumen shaft 30 and the impeller 40 may be dimensioned to any suitable diameter for intravascular applications. For example, the range of sizes may include, but is not necessarily limited to, 9 French to 30 French, although the range is typically in a range of 14 French to 24 French, and more typically in a range of 18 French to 20 French.

Figure 8A:
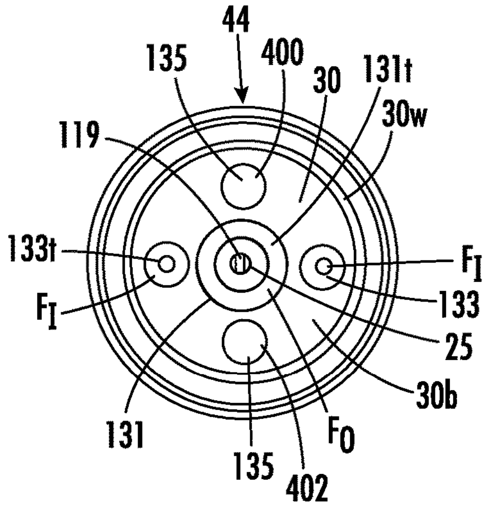
FIG. 8A is a greatly enlarged lateral section view of another embodiment of a multi-lumen shaft of a catheter blood pump according to embodiments of the present invention.

FIG. 8A illustrates an example multi-lumen shaft 30 with a plurality of internal lumens 131, 133, 135. In this view, the (blood) outflow cage 44 is also shown, but it is not part of the body 30*b* of the multi-lumen shaft 30. The body 30*b* of the multi-lumen shaft 30 can be provided as an extruded body 30*b* with multiple (substantially parallel) longitudinally extending lumens 131, 133 and the aperture 403 extending through the outer wall 30*w*. The body 30*b* can be an extruded body of polyamide or polyimide.

A separate tube 131*t*, such as a PEBAX tube, can be used to provide the lumen 131 that encases the torque cable 25 and provide at least a portion of the (fluid purge) outflow Fo path. Alternatively, the lumen 131 can be directly formed in the body 30*b* of the multi-lumen shaft 30. The at least one in-flow lumen 133 can be provided as a pair of diametrically opposed lumens as shown. The at least one in-flow lumen(s) 133 can be provided as a plurality of separate tubes or passages directly formed in the multi-lumen shaft body 30*b*. The at least one in-flow lumen 133 can be provided as polymer tubes (optionally polyimide tubes) 133*t*.

Figure 9A:
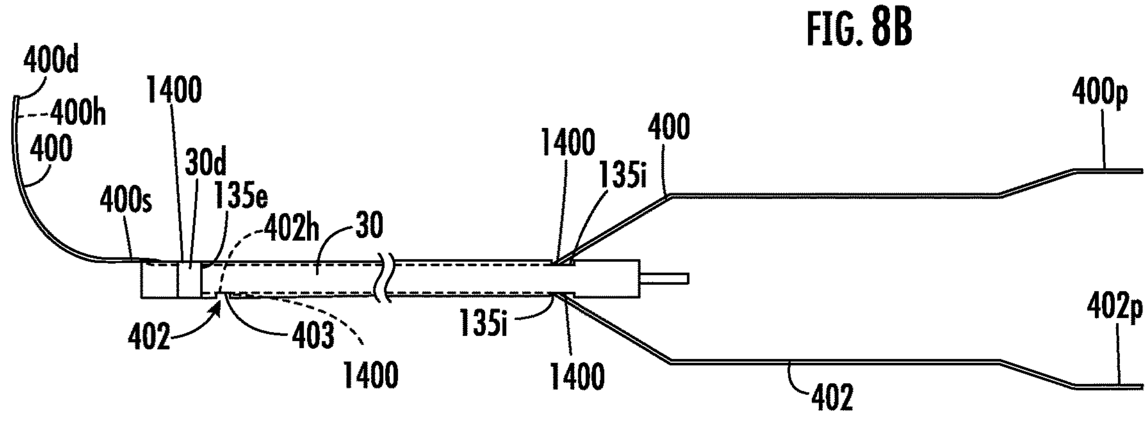
FIG. 9A is a side view of a portion of a catheter blood pump illustrating example fiberoptic pressure sensor routing along the catheter/multi-lumen shaft according to embodiments of the present invention.

As discussed above, the multi-lumen shaft 30 can also include at least one pressure sensor channel 135, shown in FIGS. 7 and 9A, as first and second diametrically opposed pressure sensor channels $\mathbf{135}_1$, $\mathbf{135}_2$, configured to hold a respective fiberoptic pressure sensor 400, 402. The pressure sensor channels 135 can be circumferentially spaced apart from the in-flow lumens 133 and can be radially aligned (at a common radius) with the in-flow lumens 133, concentric with the center lumen 131.

Figure 9B:
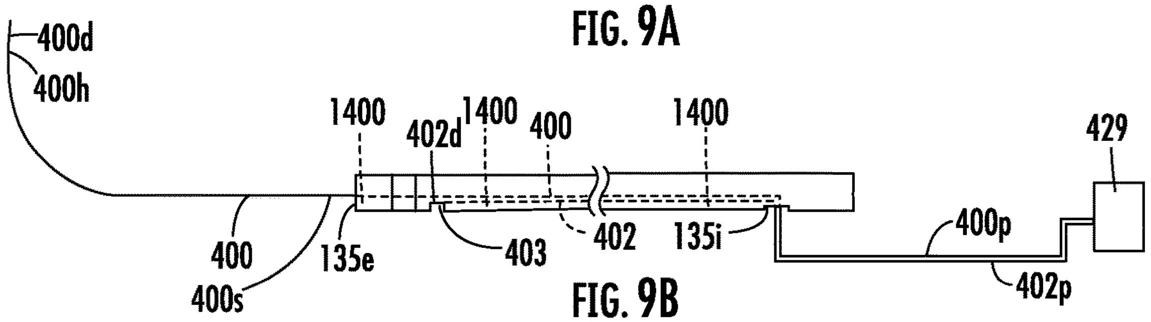
FIG. 9B is a schematic side view of a portion of a catheter blood pump illustrating another embodiment of fiberoptic pressure sensor routing along the catheter/multi-lumen shaft according to embodiments of the present invention.

As shown in FIG. 9B, the first and second fiberoptic pressure sensors 400, 402 may be held in a single lumen 135 for part of a respective length thereof, e.g., the second fiberoptic pressure sensor 402 can be held entirely in the single lumen 135 and the other can extend distally out of the single lumen 135 and each can share a respective entry point/port 135*i* or can have separate entry points (ports) (not shown).

Figure 8B:
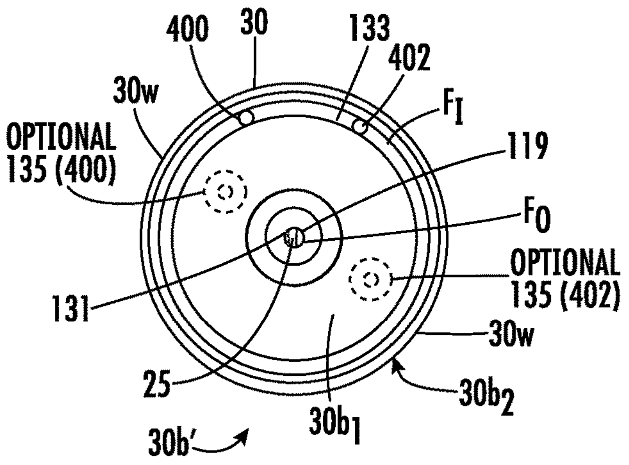
FIG. 8B is a greatly enlarged lateral section view of another embodiment of a multi-lumen shaft for a catheter blood pump according to embodiments of the present invention.

FIG. 8B illustrates another example extruded body 30*b* with an in-flow lumen 133 that is provided as an outer ring surrounding the out-flow lumen 131, arranged to provide concentric or coaxial lumen configurations. Also, FIG. 8B shows that the pressure sensors 400, 402 can be routed through the outer coaxial lumen instead of the separate parallel internal lumens 135 (shown in broken line as an optional feature of the coaxial lumen inflow, outflow paths).

The multi-lumen shaft 30 can be provided in a number of ways. For example, the multi-lumen shaft 30 can comprise an extrusion/extruded body 30*b*, 30*b*' with multiple lumens. The center lumen 131 can be a different material than the in-flow lumens 133. This configuration can be provided by a co-extrusion of separate materials extruded at the same time. In other embodiments, such as a coaxial embodiment per FIG. 8B, there can be two separate "tube" extruded bodies $\mathbf{30}b_1$, $\mathbf{30}b_2$, forming the coaxially arranged in-flow and out-flow lumens, of the same or different materials, but the two extruded tube bodies are coaxially positioned, one surrounding the other and can be extruded separately and then assembled together.

The impeller 40 can be an expandable impeller 40 or a fixed diameter impeller or a partially radially expandable impeller. See, for example, U.S. Pat. Nos. 9,028,392, 8,079,948, pending U.S. patent application Ser. No. 17/858,615 and U.S. Provisional Patent Application Ser. No. 63/353,353, the contents of which are hereby incorporated by reference as if recited in full herein.

The blood pump 10 can be sized and configured for trans-valvular use, such as for left and/or right ventricular assist procedures. By way of example only, such ventricular assist procedures may be employed in cardiac operations including, but not limited to, coronary bypass graft (CABG), cardiopulmonary bypass (CPB), open chest and closed chest (minimally invasive) surgery, bridge-to-transplant and/or failure-to-wean-from-bypass situations. It is to be readily understood, however, that the intravascular blood pump assembly and methods of the present invention are not to be limited to such applications. Moreover, while illustrated and described largely with reference to left-heart assist applications, it is to be readily understood that the principles of the present invention apply equally with regard to right-heart assist application, which are contemplated as within the scope of the present invention. These and other variations and additional features will be described throughout.

The blood pump 10 can be configured to pump blood through the outlet cage 44 at a rate in a range of 2-7 liters/minute over at least 6 days of continuous intravascular use while continuously providing biocompatible fluid to the in-flow path Fi via at least one in-flow lumen 133, then to the out-flow path Fo.

The blood pump 10 may be configured to provide axial or mixed-flow. As used herein, the term "axial flow" is deemed to include flow characteristics which include both an axial and (slight) radial component.

Figure 11A:
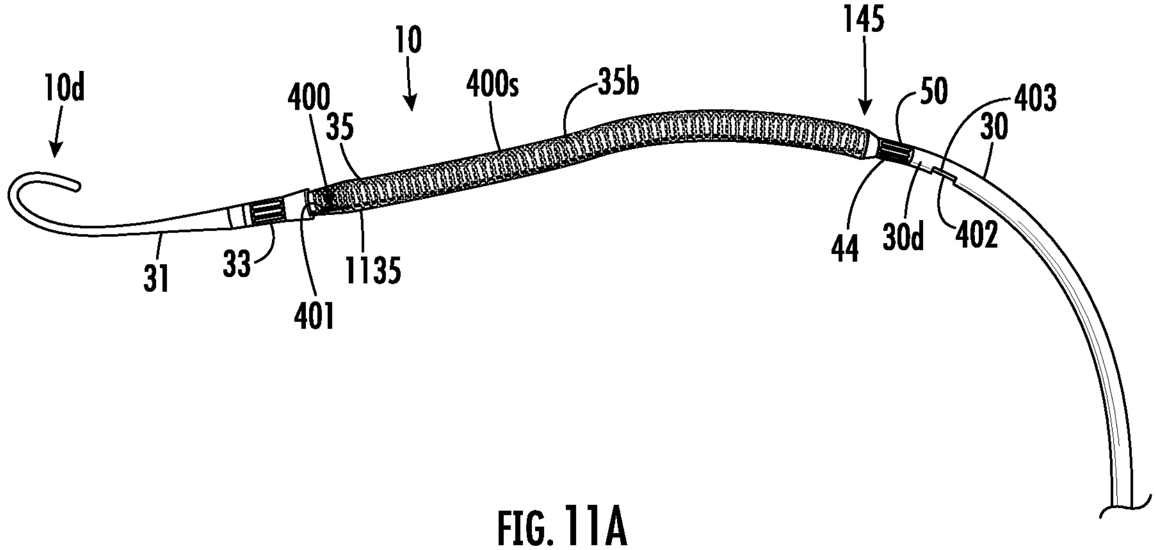
FIG. 11A is an enlarged view of a portion of a catheter blood pump according to embodiments of the present invention.
Figure 11B:
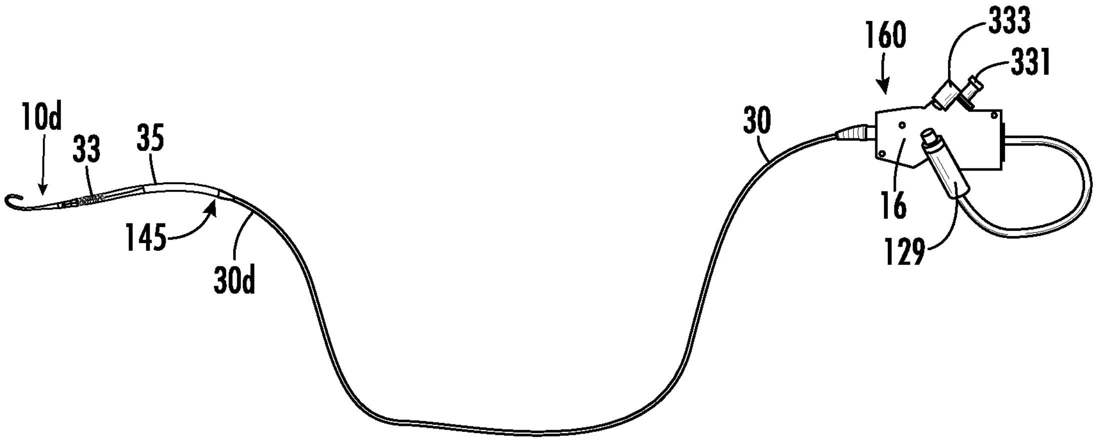
FIG. 11B is a side view of the catheter blood pump shown in FIG. 11A.

Referring to FIGS. 11A, 11B, the cannula 35 can comprise a coil 1335 encased and/or embedded in one or more layers/substrates of the cannula 35. The cannula 35 can be an extruded body with the coil 1335 encased therein. The cannula 35 can be a medical grade polymeric and/or co-polymeric extruded or molded body. The coil 1335 can be between (inside) at least one layer of a material/substrate forming the cannula body 35*b* and may be encased in a lubricious, medical grade elastomeric material. In some embodiments, the cannula 35 can have an elasticity that is greater than the catheter 30 and/or can have a durometer that is less than a durometer of the catheter 30. A distal length segment 400*s* of the first fiberoptic sensor 400 can be held between an outer surface of the coil 1335 and the outer substrate and the aperture 401 can be provided in the substrate.

The blood pump 10 can be configured to provide right and/or left heart support whereby blood is deliberately re-routed through and past the right and/or left ventricle in an effort to reduce the volume of blood to be pumped by the particular ventricle. While "unloading" the ventricles in this fashion is preferred in certain instances, it is to be understood that the pump and cannula arrangements described herein may also be employed to "preload" the ventricles. Ventricular preloading may be accomplished by positioning the outflow cage from the pump into a given ventricle such that the pump may be employed to fill or preload the ventricle with blood. This may be particularly useful with the right ventricle. On occasion, the right ventricle is not supplied with sufficient levels of blood from the right atrium such that, upon contraction, the right ventricle delivers an insufficient quantity of blood to the pulmonary artery. This may result when the right ventricle and/or right atrium are in a stressed or distorted condition during surgery. Preloading overcomes this problem by actively supplying blood into the right ventricle, thereby facilitating the delivery of blood into the pulmonary artery. The same technique can be used to preload the left ventricle and thus facilitate the delivery of blood from the left ventricle into the aorta.

The catheter blood pump system 100 can be used for positioning the catheter blood pump in the heart. It is also contemplated that such systems can reduce the costs and facilitate the use of the catheter blood pumps as an improved standard of care during medical procedures.

Pressure sensors have been proposed to monitor pressure (s) in the heart. See, e.g., U.S. Pat. Nos. 9,669,142; and 5,911,685, the contents of which are hereby incorporated by reference as if recited in full herein. However, embodiments of the present invention provide alternative, reliable, cost-effective pressure sensors for blood pump catheters.

Figure 12:
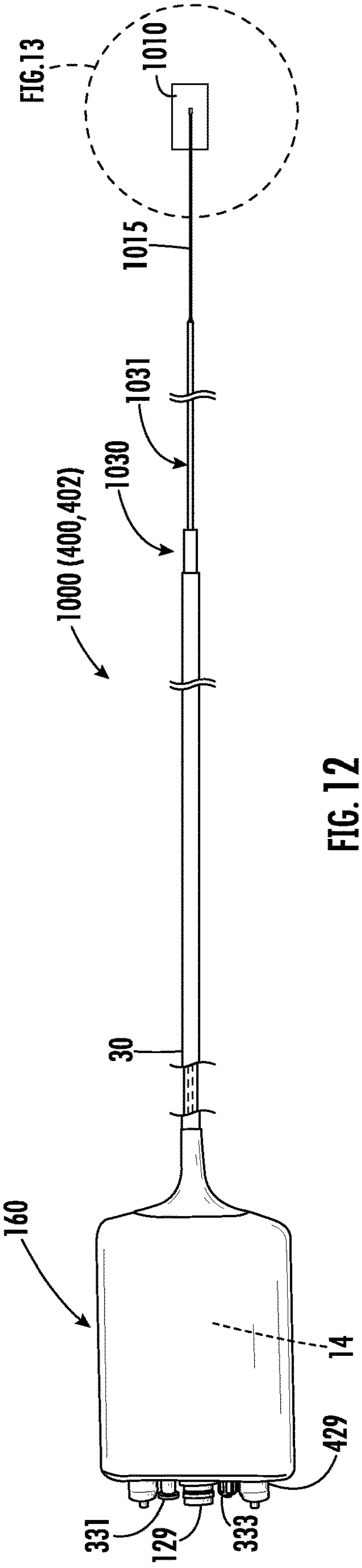
FIG. 12 is a side view of a fiberoptic pressure sensor coupled to the housing assembly of the catheter blood pump according to embodiments of the present invention.

Turning now to FIGS. 12-14, an example fiberoptic pressure sensor 1000 suitable for the fiberoptic pressure sensor 400 and/or 402 discussed above is shown. FIG. 12 shows the fiberoptic pressure sensor 1000 coupled to the housing assembly 160. Typically, there are two such fiberoptic pressure sensors 1000 terminating to the connectors 331, 333. Referring to FIG. 12, the fiberoptic pressure sensor 1000 has a glass fiber 1015 which is enclosed in a jacket 1030, that merges into a segment with a smaller diameter tube, then to the glass fiber 1015 having only a polymer/co-polymer coating 1025 providing a smaller outer diameter. A short segment of exposed glass fiber 1015*e* then extends distal of the jacket 1030 and tube 1031 and couples to the MOMS structure 1020. The short segment of exposed glass fiber 1015*e* can have a length D1 in a range of 0.003-0.05 inches. The MOMS structure 1020 can be held inside a distal sleeve 1035 along with the short segment of exposed glass fiber 1015*e*. The MOMS structure 1020 can have a length that is about the same or within +/−25% of the length of the exposed glass fiber 1015*e*. Here, the term "exposed glass fiber" means the glass fiber segment 1015*e* is devoid of an outer jacket or coating but can inside the lumen 135 and/or the sleeve 1035.

FIG. 14 shows the distal sleeve 1035 positioned about the MOMS structure 1020 and about the exposed glass fiber 1015*e* defining an open annular chamber 1033 with open spaces between the inner surface of the distal sleeve 1035 and the exposed glass fiber 1015*e* and between the outer surface of the MOMS structure 1020 and the inner surface of the distal sleeve 1035. The MOMS structure 1020 can also have a distal end 1020*d* that resides a distance D2, inside, proximal to the distal end of the distal sleeve 1035. D2 can be in a range of 0.001 and inches, in some embodiments, more typically in a range of 0.001 and 0.003 inches. The fiberoptic pressure sensor 1000 defining the proximal fiber optic sensor 402 resides inside the catheter 30, for at least a major portion of its length. The fiberoptic pressure sensor 1000 defining the distal fiber optic sensor 400 resides inside the catheter 30, for a major portion of its length. The respective skyve/aperture 401, 403, can reside adjacent the distal end 1035*d* of the distal sleeve 1035 of the corresponding fiberoptic pressure sensor 1000 providing the proximal and distal sensors 400, 402, respectively.

Figure 15:
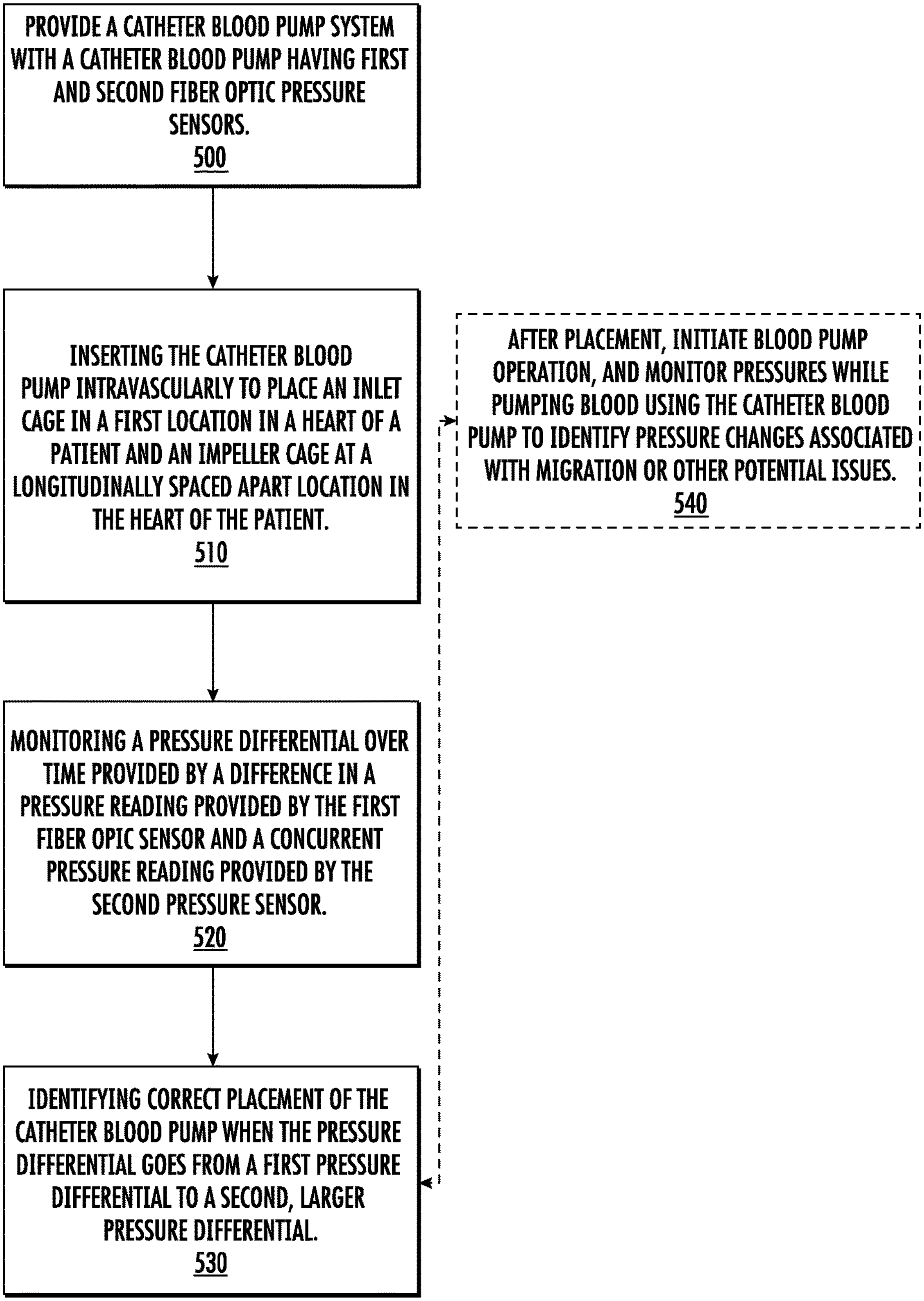
FIG. 15 is a flow chart of actions that can be used for positioning the catheter blood pump in the heart without requiring image-guided surgery according to embodiments of the present invention.

Turning now to FIG. 15, example actions for a medical procedure are shown. A catheter blood pump system with a catheter blood pump having first and second fiberoptic pressures sensors is provided (block 500). The catheter blood pump is inserted intravascularly to place an inlet cage in a first location in a heart of a patient and an impeller cage at a longitudinally spaced apart location in the heart of the patient (block 510). Concurrently obtained first and second pressures can be monitored over time to identify a pressure differential corresponding to proper intracardiac placement.

To be clear, the term "concurrently" means at substantially the same time, such as within second of each other.

The pressure differential can be provided in a number of ways. For example, a difference in a pressure P1 provided by the first fiberoptic pressure sensor and a concurrent pressure P2 provided by the second fiberoptic pressure sensor (block 520). Correct placement of the catheter blood pump is identified when a pressure difference and/or pressure differential (PD) of a defined amount is identified. The blood pump 10 during positioning is not yet operational for pumping blood (the motor does not rotate the impeller). The difference in pressure is due to anatomical position of a respective fiberoptic pressure sensor. The defined PD associated with correct positioning, can be relative to a first (baseline) pressure difference PD1 (typically at a common or similar pressure) to a second, larger pressure difference PD2 (block 530) indicating the first fiberoptic pressure sensor is in the LV (left ventricle) and the second fiberoptic pressure sensor is above the aortic valve, typically in the ascending aorta. The pressure difference PD can be provided in any suitable manner, such as a ratio of current pressure measurements by the two fiberoptic pressure sensors 400, 402: P1/P2 or a difference (P1-P2) of two current pressure measurements provided by the two fiberoptic pressure sensors or in other relevant calculations.

After placement, initiate blood pump operation, and the system can continue to monitor pressures P1 and P2 while pumping blood using the catheter blood pump to identify pressure changes associated with migration or other potential issues (block 540).

Figure 16:
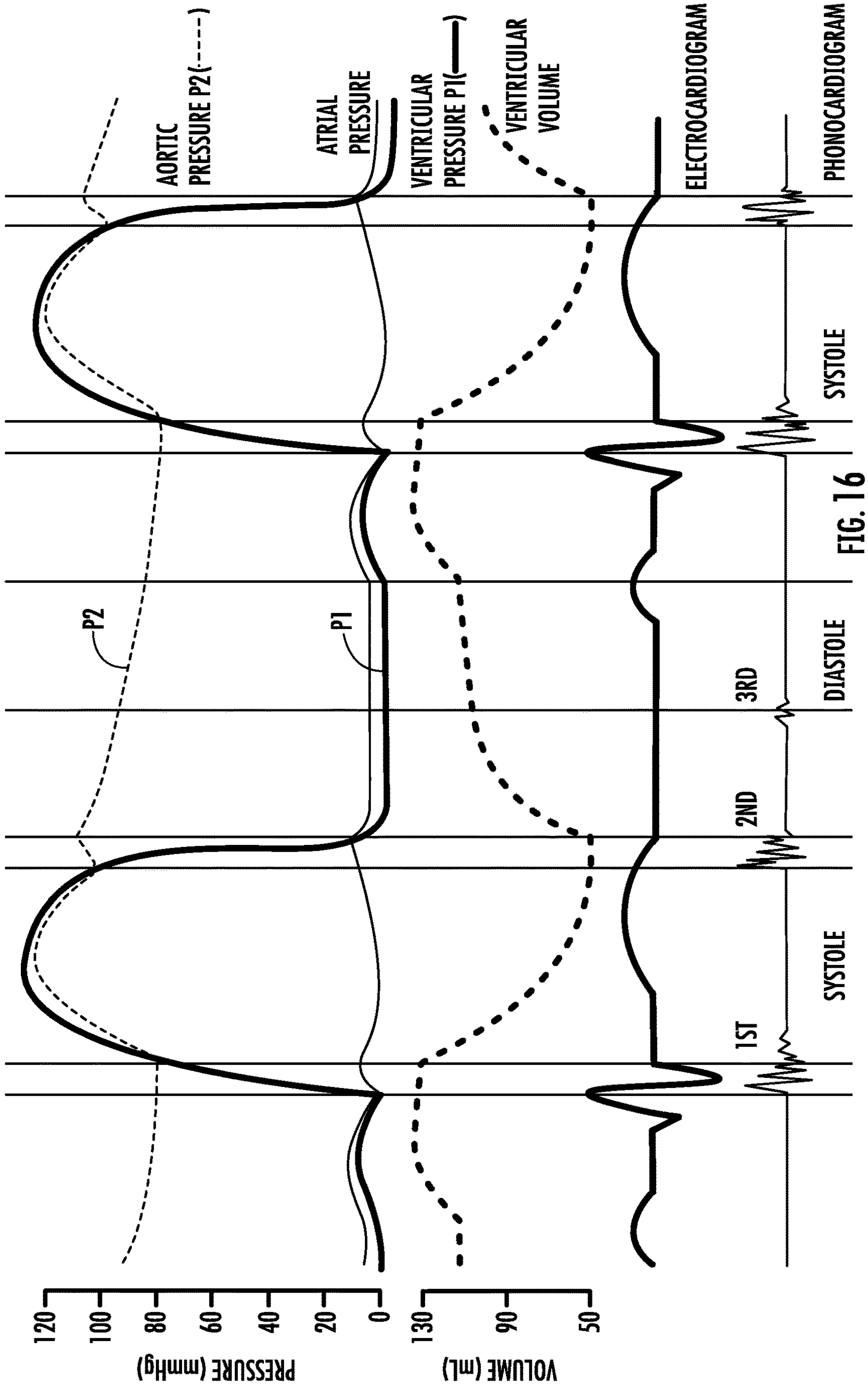
FIG. 16 is a graph of pressures occurring during a normal cardiac cycle.

FIG. 16 illustrates aortic and ventricular pressures and differentials over a cardiac cycle of a normal heart. During systole, pressures P1 and P2 are similar but during diastole, the ventricular pressure P1 drops dramatically, to about 0 mmHg, relative to the aortic pressure P2, which decreases from peak pressure of about 120 mmHg to a range of about 100-80 mmHg, e.g., typically providing a pressure difference of at least about 60 mmHg, typically about 80 mmHg.

In the drawings and specification, there have been disclosed embodiments of the invention and, although specific terms are employed, they are used in a generic and descriptive sense only and not for purposes of limitation, the scope of the invention being set forth in the following claims.

Thus, the foregoing is illustrative of the present invention and is not to be construed as limiting thereof. More particularly, the workflow steps may be carried out in a different manner, in a different order and/or with other workflow steps or may omit some or replace some workflow steps with other steps. Although a few exemplary embodiments of this invention have been described, those skilled in the art will readily appreciate that many modifications are possible in the exemplary embodiments without materially departing from the novel teachings and advantages of this invention.

Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

It is to be understood that the disclosure describes a few embodiments and that many variations of the invention can easily be devised by those skilled in the art after reading this disclosure and that the scope of the present invention is to be determined by the following claims.

What is claimed:

1. A catheter blood pump, comprising:

a housing comprising inflow and outflow ports and at least one fiberoptic pressure sensor connector;

a multi-lumen catheter coupled, at a proximal end thereof, to the housing and comprising an inflow liquid flow path coupled to the inflow port and an outflow liquid flow path coupled to the outflow port;

an impeller assembly disposed adjacent to a distal end portion of the multi-lumen catheter, the impeller assembly comprising an impeller within an impeller cage, wherein the impeller cage comprises a plurality of struts that are circumferentially spaced apart and a plurality of windows, at least one window of the plurality of windows positioned between a pair of the plurality of struts;

a cannula coupled to a distal end portion of the impeller assembly;

an inlet cage provided by or coupled to a distal end portion of the cannula; and first and second fiberoptic pressure sensors, wherein each of the first and second fiberoptic pressure sensors comprises at least one optical fiber and a sensor head, wherein the at least one optical fiber of each of the first and second fiberoptic pressure sensors have a proximal end portion coupled to the at least one fiberoptic pressure sensor connector, and wherein at least a portion of each of the at least one optical fiber of each of the first and second fiberoptic pressure sensors extends longitudinally along and internal to an outer wall of the multi-lumen catheter, wherein the at least one optical fiber of the first fiberoptic pressure sensor is longer than the at least one optical fiber of the second fiberoptic pressure sensor and comprises a first segment that extends out of a distal end portion of the multi-lumen catheter, along one strut of the plurality of circumferentially spaced apart struts of the impeller cage, then merges into a second more distal segment that extends longitudinally along the cannula to position the sensor head thereof proximal to the inlet cage, and wherein the second fiberoptic pressure sensor positions the sensor head thereof proximal to the plurality of windows of the impeller cage.

2. The catheter blood pump of claim 1, wherein the multi-lumen catheter comprises a central lumen and one or more peripheral lumens disposed radially outward of the central lumen.

3. A catheter blood pump, comprising:

a housing comprising inflow and outflow ports and at least one fiberoptic pressure sensor connector;

a multi-lumen catheter coupled, at a proximal end thereof, to the housing and comprising an inflow liquid flow path coupled to the inflow port and an outflow liquid flow path coupled to the outflow port;

an impeller assembly disposed adjacent to a distal end portion of the multi-lumen catheter, the impeller assembly comprising an impeller within an impeller cage, wherein the impeller cage comprises a plurality of struts that are circumferentially spaced apart and a plurality of windows, at least one window of the plurality of windows positioned between a pair of the plurality of struts;

a cannula coupled to a distal end portion of the impeller assembly;

an inlet cage provided by or coupled to a distal end portion of the cannula; and first and second fiberoptic pressure sensors, wherein each of the first and second fiberoptic pressure sensors comprises at least one optical fiber and a sensor head, wherein the at least one optical fiber of each of the first and second fiberoptic pressure sensors have a proximal end portion coupled to the at least one fiberoptic pressure sensor connector, and wherein at least a portion of each of the at least one optical fiber of each of the first and second fiberoptic pressure sensors extends longitudinally along and internal to an outer wall of the multi-lumen catheter, wherein the at least one optical fiber of the first fiberoptic pressure sensor is longer than the at least one optical fiber of the second fiberoptic pressure sensor and comprises a first segment that extends out of a distal end portion of the multi-lumen catheter, along one strut of the plurality of circumferentially spaced apart struts of the impeller cage, then merges into a second more distal segment that extends longitudinally along the cannula to position the sensor head thereof proximal to the inlet cage, and wherein the second fiberoptic pressure sensor positions the sensor head thereof proximal to the plurality of windows of the impeller cage, wherein the multi-lumen catheter comprises a central lumen and one or more peripheral lumens disposed radially outward of the central lumen, and wherein the one or more peripheral lumens comprises a first pressure sensor lumen and a second pressure sensor lumen that is spaced apart from the first pressure sensor lumen, wherein the at least one optical fiber of the first fiberoptic pressure sensor enters the first pressure sensor lumen via a first entry port in the outer wall of the multi-lumen catheter, distal to a proximal end of the multi-lumen catheter and proximal to a medial segment of the multi-lumen catheter, and wherein the at least one optical fiber of the second fiberoptic pressure sensor enters the second pressure sensor lumen via a second entry port in the outer wall of the multi-lumen catheter, distal to the proximal end of the multi-lumen catheter and proximal to a medial segment of the multi-lumen catheter.

4. The catheter blood pump of claim 3, wherein the first and the second entry ports reside a distance in a range of 1 mm to 3 inches from the proximal end of the multi-lumen catheter.

5. The catheter blood pump of claim 3, further comprising:

a first adhesive segment coupled to a sub-length of the at least one optical fiber of the first fiberoptic pressure sensor adjacent to the first entry port, wherein the first adhesive segment has a length in a range of 0.1 inches to about 2 inches; and a second adhesive segment coupled to a sub-length of the at least one optical fiber of the second fiberoptic pressure sensor adjacent to the second entry port, wherein the second adhesive segment has a length in a range of 0.1 inches to about 2 inches.

6. The catheter blood pump of claim 1, wherein the sensor head of the second fiberoptic pressure sensor is held in a distal end portion of the multi-lumen catheter and is in fluid communication with external environmental conditions proximal to the windows of the impeller cage.

7. The catheter blood pump of claim 6, wherein the sensor head of the second fiberoptic pressure sensor resides a distance in a range of 0.01 inches and 0.25 inches from a proximal end of the windows of the impeller cage.

8. The catheter blood pump of claim 1, wherein the sensor head of the second fiberoptic pressure sensor is exposed to environmental conditions through an aperture in the outer wall of the distal end portion of the multi-lumen catheter.

9. The catheter blood pump of claim 8, further comprising an adhesive segment proximal to the aperture of the multi-lumen catheter, wherein the sensor head of the second fiberoptic pressure sensor is free of adhesive and is adjacent the aperture in the outer wall of the multi-lumen catheter.

10. The catheter blood pump of claim 1, further comprising a control circuit operatively coupled to the at least one fiberoptic pressure sensor connector and configured to obtain concurrent pressure measurement signals provided by the first and second fiberoptic pressure sensors.

11. A catheter blood pump, comprising:

a housing comprising inflow and outflow ports and at least one fiberoptic pressure sensor connector;

a multi-lumen catheter coupled, at a proximal end thereof, to the housing and comprising an inflow liquid flow path coupled to the inflow port and an outflow liquid flow path coupled to the outflow port;

an impeller assembly disposed adjacent to a distal end portion of the multi-lumen catheter, the impeller assembly comprising an impeller within an impeller cage, wherein the impeller cage comprises a plurality of struts that are circumferentially spaced apart and a plurality of windows, at least one window of the plurality of windows positioned between a pair of the plurality of struts;

a cannula coupled to a distal end portion of the impeller assembly;

an inlet cage provided by or coupled to a distal end portion of the cannula;

first and second fiberoptic pressure sensors, wherein each of the first and second fiberoptic pressure sensors comprises at least one optical fiber and a sensor head, wherein the at least one optical fiber of each of the first and second fiberoptic pressure sensors have a proximal end portion coupled to the at least one fiberoptic pressure sensor connector, and wherein at least a portion of each of the at least one optical fiber of each of the first and second fiberoptic pressure sensors extends longitudinally along and internal to an outer wall of the multi-lumen catheter, wherein the at least one optical fiber of the first fiberoptic pressure sensor is longer than the at least one optical fiber of the second fiberoptic pressure sensor and comprises a first segment that extends out of a distal end portion of the multi-lumen catheter, along one strut of the plurality of circumferentially spaced apart struts of the impeller cage, then merges into a second more distal segment that extends longitudinally along the cannula to position the sensor head thereof proximal to the inlet cage, and wherein the second fiberoptic pressure sensor positions the sensor head thereof proximal to the plurality of windows of the impeller cage; and a control circuit operatively coupled to the at least one fiberoptic pressure sensor connector and configured to obtain concurrent pressure measurement signals provided by the first and second fiberoptic pressure sensors, wherein the control circuit comprises pressure sensor electronics that communicate with the first and second fiberoptic pressure sensors, and wherein the control circuit is configured to identify correct placement of the inlet cage and impeller cage based on a pressure differential of concurrent pressure measurements from the first and second fiberoptic pressure sensors.

12. The catheter blood pump of claim 1, wherein the multi-lumen catheter comprises an inflow flush fluid lumen providing at least part of the inflow liquid flow path and an outflow flush fluid lumen providing at least part of the outflow liquid flow path, wherein the inflow port is provided by a flush fluid intake connector extending outward from the housing that intakes flush fluid from a flush fluid source, wherein the outflow port is provided by a flush fluid waste connector that extends outward from the housing and directs outflow flush fluid to a collection device, and wherein the housing further comprises a flush fluid manifold that is in fluid communication with the flush fluid intake connector, the flush fluid waste connector, the inflow flush fluid lumen, and the outflow flush fluid lumen whereby the manifold is configured to direct flush fluid from the flush fluid intake connector to the inflow flush fluid lumen and direct flush fluid from the outflow flush fluid lumen to the flush fluid waste connector.

13. A catheter blood pump, comprising:

a housing comprising inflow and outflow ports and at least one fiberoptic pressure sensor connector;

a multi-lumen catheter coupled, at a proximal end thereof, to the housing and comprising an inflow liquid flow path coupled to the inflow port and an outflow liquid flow path coupled to the outflow port;

an impeller assembly disposed adjacent to a distal end portion of the multi-lumen catheter, the impeller assembly comprising an impeller within an impeller cage, wherein the impeller cage comprises a plurality of struts that are circumferentially spaced apart and a plurality of windows, at least one window of the plurality of windows positioned between a pair of the plurality of struts;

a cannula coupled to a distal end portion of the impeller assembly;

an inlet cage provided by or coupled to a distal end portion of the cannula; and first and second fiberoptic pressure sensors, wherein each of the first and second fiberoptic pressure sensors comprises at least one optical fiber and a sensor head, wherein the at least one optical fiber of each of the first and second fiberoptic pressure sensors have a proximal end portion coupled to the at least one fiberoptic pressure sensor connector, and wherein at least a portion of each of the at least one optical fiber of each of the first and second fiberoptic pressure sensors extends longitudinally along and internal to an outer wall of the multi-lumen catheter, wherein the at least one optical fiber of the first fiberoptic pressure sensor is longer than the at least one optical fiber of the second fiberoptic pressure sensor and comprises a first segment that extends out of a distal end portion of the multi-lumen catheter, along one strut of the plurality of circumferentially spaced apart struts of the impeller cage, then merges into a second more distal segment that extends longitudinally along the cannula to position the sensor head thereof proximal to the inlet cage, and wherein the second fiberoptic pressure sensor positions the sensor head thereof proximal to the plurality of windows of the impeller cage, wherein the multi-lumen catheter comprises an inflow flush fluid lumen providing at least part of the inflow liquid flow path and an outflow flush fluid lumen providing at least part of the outflow liquid flow path, wherein the inflow port is provided by a flush fluid intake connector extending outward from the housing that intakes flush fluid from a flush fluid source, wherein the outflow port is provided by a flush fluid waste connector that extends outward from the housing and directs outflow flush fluid to a collection device, and wherein the housing further comprises a flush fluid manifold that is in fluid communication with the flush fluid intake connector, the flush fluid waste connector, the inflow flush fluid lumen, and the outflow flush fluid lumen whereby the manifold is configured to direct flush fluid from the flush fluid intake connector to the inflow flush fluid lumen and direct flush fluid from the outflow flush fluid lumen to the flush fluid waste connector, wherein the flush fluid intake connector and the flush fluid waste connector are parallel and extend at an angle between 30-75 degrees from a sidewall of the housing.

14. The catheter blood pump of claim 1, wherein the sensor head of the first fiberoptic pressure sensor is positioned inside an outer wall of the cannula and is exposed to environmental conditions via an aperture in the outer wall of the cannula.

15. The catheter blood pump of claim 1, wherein the second fiberoptic pressure sensor is configured to that the sensor head thereof is inside the multi-lumen catheter.

16. The catheter blood pump of claim 1, further comprising an adhesive segment coupled to a portion of the at least one optical fiber of the first fiberoptic pressure sensor and a distal end portion of a wall bounding a lumen of the multi-lumen catheter holding the portion of the at least one optical fiber of the first fiberoptic pressure sensor, wherein the adhesive segment has a length in a range of 0.1 inches to about 2 inches is configured to provide a fluid barrier.

17. The catheter blood pump of claim 1, further comprising a first adhesive segment coupled to a first portion of the at least one optical fiber of the first fiberoptic pressure sensor at an exit location from the multi-lumen catheter and a second adhesive segment longitudinally spaced apart from and proximal to the first adhesive segment, also coupled to the at least one optical fiber of the first fiberoptic pressure sensor, wherein the first and second adhesive segments reside inside a lumen of the multi-lumen catheter holding the at least one optical fiber of the first fiberoptic pressure sensor.

18. The catheter blood pump of claim 1, wherein the at least one fiberoptic pressure sensor connector is a single fiberoptic pressure sensor connector whereby the first and second fiberoptic pressure sensors have respective proximal ends that are coupled to the single fiberoptic pressure sensor connector.

19. The catheter blood pump of claim 1, wherein the second segment of the at least one optical fiber of the first fiberoptic pressure sensor that extends along the cannula is sandwiched between an inner wall and outer wall of the cannula.

20. The catheter blood pump of claim 1, wherein the housing is a motor assembly housing and encloses a motor in the housing, and wherein the catheter blood pump further comprises a flexible drive cable operatively coupled, at a proximal end thereof, to the motor, the flexible drive cable extending from the motor into a central lumen of the multi-lumen catheter, and wherein the impeller is operatively coupled to a distal end portion of the flexible drive cable.

21. The catheter blood pump of claim 1, wherein the multi-lumen catheter comprises a coaxial arrangement of inflow and outflow flush fluid lumens.

22. The catheter blood pump of claim 1, further comprising a heat shrink outer layer residing distal to the multi-lumen catheter and covering a first segment of the first fiberoptic pressure sensor.

23. The catheter blood pump of claim 1, wherein a sensor head of the second fiberoptic pressure sensor resides in an open channel of a lumen of the multi-lumen catheter, and wherein a segment of adhesive resides proximal to the sensor head in the lumen to define a fluid barrier.

24. A catheter blood pump, comprising:

a housing comprising inflow and outflow ports and at least one fiberoptic pressure sensor connector;

a multi-lumen catheter coupled, at a proximal end thereof, to the housing and comprising an inflow liquid flow path coupled to the inflow port and an outflow liquid flow path coupled to the outflow port;

an impeller assembly disposed adjacent to a distal end portion of the multi-lumen catheter, the impeller assembly comprising an impeller within an impeller cage, wherein the impeller cage comprises a plurality of struts that are circumferentially spaced apart and a plurality of windows, at least one window of the plurality of windows positioned between a pair of the plurality of struts;

a cannula coupled to a distal end portion of the impeller assembly;

an inlet cage provided by or coupled to a distal end portion of the cannula; and first and second fiberoptic pressure sensors, wherein each of the first and second fiberoptic pressure sensors comprises at least one optical fiber and a sensor head, wherein the at least one optical fiber of each of the first and second fiberoptic pressure sensors have a proximal end portion coupled to the at least one fiberoptic pressure sensor connector, and wherein at least a portion of each of the at least one optical fiber of each of the first and second fiberoptic pressure sensors extends longitudinally along and internal to an outer wall of the multi-lumen catheter, wherein the at least one optical fiber of the first fiberoptic pressure sensor is longer than the at least one optical fiber of the second fiberoptic pressure sensor and comprises a first segment that extends out of a distal end portion of the multi-lumen catheter, along one strut of the plurality of circumferentially spaced apart struts of the impeller cage, then merges into a second more distal segment that extends longitudinally along the cannula to position the sensor head thereof proximal to the inlet cage, and wherein the second fiberoptic pressure sensor positions the sensor head thereof proximal to the plurality of windows of the impeller cage, wherein the sensor head of the second fiberoptic pressure sensor has a MOMS structure that is surrounded by an open annular channel free of adhesive.

25. A catheter blood pump, comprising:

a housing comprising inflow and outflow ports and at least one fiberoptic pressure sensor connector;

a multi-lumen catheter coupled, at a proximal end thereof, to the housing and comprising an inflow liquid flow path coupled to the inflow port and an outflow liquid flow path coupled to the outflow port;

an impeller assembly disposed adjacent to a distal end portion of the multi-lumen catheter, the impeller assembly comprising an impeller within an impeller cage, wherein the impeller cage comprises a plurality of struts that are circumferentially spaced apart and a plurality of windows;

a cannula coupled to a distal end portion of the impeller assembly;

an inlet cage provided by or coupled to a distal end portion of the cannula; and a first fiberoptic pressure sensor and a second fiberoptic pressure sensor, wherein each of the first fiberoptic pressure sensor and the second fiberoptic pressure sensor comprises at least one optical fiber and a sensor head, wherein the at least one optical fiber of each of the first and second fiberoptic pressure sensors has a proximal end portion coupled to the at least one fiberoptic pressure sensor connector, and wherein at least a portion of each of the at least one optical fiber of each of the first and second fiberoptic pressure sensors extends longitudinally along and internal to an outer wall of the multi-lumen catheter, wherein the at least one optical fiber of the first fiberoptic pressure sensor is longer than the at least one optical fiber of the second fiberoptic pressure sensor and comprises a first segment that extends out of a distal end portion of the multi-lumen catheter, along one strut of the plurality of struts of the impeller cage, then merges into a second more distal segment that extends longitudinally along the cannula to position the sensor head thereof adjacent to the inlet cage, and wherein the sensor head of the second fiberoptic pressure sensor is positioned proximal to windows of the impeller cage with the sensor head of the second fiberoptic pressure sensor in an open channel of a lumen of the multi-lumen catheter, and wherein a first adhesive segment resides proximal to the sensor head in the lumen to define a fluid barrier.

26. The catheter blood pump of claim 25, further comprising a second adhesive segment in the lumen longitudinally spaced apart from the first adhesive segment.

27. The catheter blood pump of claim 26, wherein the first adhesive segment has a different longitudinal extent and/or a different flexibility from the second adhesive segment.

28. A catheter blood pump, comprising:

a housing comprising inflow and outflow ports and at least one fiberoptic pressure sensor connector;

a multi-lumen catheter coupled, at a proximal end thereof, to the housing and comprising an inflow liquid flow path coupled to the inflow port and an outflow liquid flow path coupled to the outflow port;

an impeller assembly disposed adjacent to a distal end portion of the multi-lumen catheter, the impeller assembly comprising an impeller within an impeller cage, wherein the impeller cage comprises a plurality of struts that are circumferentially spaced apart and a plurality of windows;

a cannula coupled to a distal end portion of the impeller assembly;

an inlet cage provided by or coupled to a distal end portion of the cannula; and a first fiberoptic pressure sensor and a second fiberoptic pressure sensor, wherein each of the first fiberoptic pressure sensor and the second fiberoptic pressure sensor comprises at least one optical fiber and a sensor head, wherein the at least one optical fiber of each of the first and second fiberoptic pressure sensors has a proximal end portion coupled to the at least one fiberoptic pressure sensor connector, and wherein at least a portion of each of the at least one optical fiber of each of the first and second fiberoptic pressure sensors extends longitudinally along and internal to an outer wall of the multi-lumen catheter, wherein the at least one optical fiber of the first fiberoptic pressure sensor is longer than the at least one optical fiber of the second fiberoptic pressure sensor and comprises a first segment that extends out of a distal end portion of the multi-lumen catheter, along one strut of the plurality of struts of the impeller cage, then merges into a second more distal segment that extends longitudinally along the cannula to position the sensor head thereof adjacent to the inlet cage, wherein the sensor head of the second fiberoptic pressure sensor is positioned proximal to windows of the impeller cage with the sensor head of the second fiberoptic pressure sensor in an open channel of a lumen of the multi-lumen catheter, and wherein a first adhesive segment resides proximal to the sensor head in the lumen to define a fluid barrier, and wherein the sensor head of the second fiberoptic pressure sensor has a MOMS structure that is surrounded by an open annular channel free of adhesive.

* * * * *